(12) United States Patent
Hine et al.

(10) Patent No.: US 12,017,083 B2
(45) Date of Patent: Jun. 25, 2024

(54) ADJUSTABLE LEAD SYSTEMS FOR CARDIAC SEPTAL WALL IMPLANTATION

(71) Applicant: Medtronic, Inc., Minneapolis, MN (US)

(72) Inventors: Douglas S. Hine, Forest Lake, MN (US); Zhongping Yang, Woodbury, MN (US); William J. Clemens, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 540 days.

(21) Appl. No.: 17/070,361

(22) Filed: Oct. 14, 2020

(65) Prior Publication Data

US 2021/0106839 A1    Apr. 15, 2021

Related U.S. Application Data

(60) Provisional application No. 62/948,366, filed on Dec. 16, 2019, provisional application No. 62/914,937, filed on Oct. 14, 2019.

(51) Int. Cl.
| | | |
|---|---|---|
| *A61N 1/39* | (2006.01) | |
| *A61N 1/05* | (2006.01) | |
| *A61N 1/362* | (2006.01) | |

(52) U.S. Cl.
CPC ....... *A61N 1/39622* (2017.08); *A61N 1/0573* (2013.01); *A61N 1/362* (2013.01)

(58) Field of Classification Search
CPC .. A61N 1/39622; A61N 1/0573; A61N 1/362; A61N 1/0558; A61N 1/057; A61N 1/37518

USPC .............................................................. 607/4
See application file for complete search history.

(56) References Cited

U.S. PATENT DOCUMENTS

| | | | |
|---|---|---|---|
| 4,452,254 A * | 6/1984 | Goldberg ............. | A61N 1/0573 607/127 |
| 6,070,104 A | 5/2000 | Hine et al. | |
| 7,164,948 B2 | 1/2007 | Struble et al. | |
| 7,386,351 B2 | 6/2008 | Hine et al. | |
| 7,499,758 B2 * | 3/2009 | Cates ...................... | A61N 1/05 607/126 |
| 7,945,337 B2 * | 5/2011 | Brabec ................. | A61N 1/0568 607/122 |
| 9,579,501 B2 * | 2/2017 | Shuros ................. | A61N 1/0573 |
| 10,092,744 B2 | 10/2018 | Sommer et al. | |
| 10,315,028 B2 | 6/2019 | Sommer et al. | |
| 10,335,589 B2 | 7/2019 | Kim | |
| 10,391,305 B2 | 8/2019 | Asleson et al. | |
| 10,426,952 B2 * | 10/2019 | Kveen ................. | A61N 1/37205 |
| 2003/0083727 A1 * | 5/2003 | Casavant ............. | A61N 1/0573 607/122 |

(Continued)

*Primary Examiner* — Joseph M Dietrich
*Assistant Examiner* — Michael T. Holtzclaw
(74) *Attorney, Agent, or Firm* — Mueting Raasch Group

(57) ABSTRACT

An implantable lead system may include an adjustable lead assembly. The lead assembly may include a fixation member and an implantable lead slidably coupled to and rotatable relative to the fixation member. The implantable lead system may include a telescoping delivery system. The delivery system may include an outer catheter and an inner catheter slidably coupled to and rotatable relative to the outer catheter. The lead assembly may be implanted in a cardiac septal wall through the delivery assembly.

16 Claims, 28 Drawing Sheets

(56) References Cited

U.S. PATENT DOCUMENTS

| | | | |
|---|---|---|---|
| 2004/0116993 A1* | 6/2004 | Clemens | A61N 1/056 607/122 |
| 2004/0230276 A1* | 11/2004 | Marshall | A61N 1/0568 607/122 |
| 2005/0085886 A1* | 4/2005 | Hess | A61N 1/0565 607/127 |
| 2009/0259272 A1* | 10/2009 | Reddy | A61N 1/0573 607/9 |
| 2012/0158108 A1* | 6/2012 | Foster | A61N 1/0573 607/119 |
| 2012/0245665 A1* | 9/2012 | Friedman | A61N 1/0573 607/122 |
| 2012/0253444 A1* | 10/2012 | Arnholt | A61N 1/05 607/116 |
| 2014/0018892 A1* | 1/2014 | Dahlberg | A61N 1/056 607/116 |

\* cited by examiner

ADJUSTABLE LEAD SYSTEMS FOR CARDIAC SEPTAL WALL IMPLANTATION

The present application claims the benefit of U.S. Provisional Application No. 62/914,937, filed Oct. 14, 2019, and U.S. Provisional Application No. 62/948,366, filed Dec. 16, 2019, each of which are incorporated herein by reference in their entireties.

The present technology is generally related to implantable medical devices, systems, and methods. In particular, the present technology is related to implantable lead systems and delivery for cardiac sensing and therapy.

Implantable medical devices (IMDs), such as cardiac pacemakers or implantable cardioverter defibrillators, deliver therapeutic stimulation to patients' hearts. Patients with a conduction system abnormality, such as poor atrioventricular (AV) node conduction or poor sinoatrial (SA) node function, may receive an IMD, such as a pacemaker, to restore a more normal heart rhythm and AV synchrony. Some types of IMDs, such as cardiac pacemakers, implantable cardioverter-defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart and control the delivery of therapeutic stimulation to the heart based on the sensing.

Existing pacing techniques involve pacing one or more of the four chambers of patient's heart 10, including the right atrium (RA) 12, right ventricle (RV) 14, left ventricle (LV) 16, and left atrium (LA) 18 all of which are shown in the anterior view of a frontal section of patient's heart 10 illustrated in FIG. 1. Some therapeutic pacing techniques involve the cardiac conduction system. The cardiac conduction system, like a "superhighway," may be described as quickly conducting electrical pulses whereas pacing cardiac muscle tissue may slowly conduct electrical pulses, like "traveling on a dirt road." The cardiac conduction system includes SA node 20, atrial internodal tracts 22, 23, 24 (i.e., anterior internodal 22, middle internodal 23, and posterior internodal 24), atrioventricular node (AV node) 26, His bundle 28 (also known as the atrioventricular bundle or bundle of His), and bundle branches including the left bundle branch (LBB) 30 and the right bundle branch (RBB) 32. FIG. 1 also shows the arch of aorta 34 and Bachman's bundle 36.

The SA node 20, located at the junction of the superior vena cava 38 and RA 12, is considered to be the natural pacemaker of the heart since it continuously and repeatedly emits electrical impulses. The electrical impulse spreads through the muscles of RA 12 to LA 18 to cause synchronous contraction of the atria. Electrical impulses are also carried through atrial internodal tracts to AV node 26—the sole connection between the atria and the ventricles.

Conduction through the AV nodal tissue takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the bundle of His.

His bundle 28 is located in the membranous atrioventricular septum near the annulus of the tricuspid valve. The tricuspid valve 42 is between the RA 12 and the RV 14. His bundle 28 splits into the LBB 30 and RBB 32 and are formed of specialized fibers called "Purkinje fibers" 40. Purkinje fibers 40 may be described as rapidly conducting an action potential down the ventricular septum, spreading the depolarization wavefront quickly through the remaining ventricular myocardium, and producing a coordinated contraction of the ventricular muscle mass.

The techniques of this disclosure generally relate to implantable lead systems including adjustable fixation lead assemblies for cardiac therapy and telescoping catheter delivery assemblies for septal wall implantation. Adjustable fixation lead assemblies may include a fixation member slidably coupled to a lead. Adjustable fixation lead assemblies may facilitate implantation of the lead to an appropriate depth in a septal wall of a patient's heart. The lead may include multiple electrodes. Multiple electrodes may facilitate pacing of more than one region of the patient's heart. Lead assemblies may be delivered to the septal wall using telescoping catheter delivery assemblies. Telescoping catheter delivery assemblies may include an outer catheter and an inner catheter each including a curved region. Telescoping catheter delivery assemblies may facilitate perpendicular positioning of the lead into the septal wall.

In one aspect, the present disclosure provides an implantable lead system including a fixation member. The fixation member includes a proximal portion, a distal portion, a fixation element coupled to the distal portion, and an elongate body extending between the proximal portion and the distal portion. The fixation element is configured to attach to a septal wall of a patient's heart. The elongate body is configured to transfer torque from the proximal portion to the distal portion. The implantable lead system also includes an implantable lead. The implantable lead includes a proximal portion, a distal portion, a lead body extending between the proximal portion and the distal portion, and an electrode coupled to the distal portion. The distal portion is configured to be at least partially inserted into the septal wall. The electrode is configured to be implanted at an implantation site in the septal wall. The implantable lead is slidably coupled to and rotatable relative to the fixation member. The implantable lead system may be described as adjustable to accommodate different anatomy of the patient's heart, such as different septal wall thicknesses.

In another aspect, the present disclosure provides a lead delivery system including an outer catheter. The outer catheter includes a proximal portion, a distal portion, and an elongate body extending between the proximal portion and the distal portion, the elongate body defining a lumen. The elongate body defines a first curved region configured to position the distal portion of the outer catheter in the right atrium or the right ventricle of a patient's heart when the elongate body extends through the superior vena cava of the patient's heart. The lead delivery system also includes an inner catheter. The inner catheter includes a proximal portion, a distal portion, and an elongate body extending between the proximal portion and the distal portion. The elongate body defines a lumen. The inner catheter is receivable into the lumen of the outer catheter. The inner catheter is slidably coupled to and rotatable relative to the outer catheter. The elongate body of the inner catheter defines a second curved region configured to move the distal portion of the inner catheter proximate to a septal wall of the patient's heart toward a perpendicular position relative to the septal wall. The lead delivery system may be described as telescoping to accommodate various heart anatomies and sizes when delivering a lead.

In another aspect, the present disclosure provides a method for delivering an implantable lead system including advancing a telescoping catheter delivery assembly into to the right atrium or the right ventricle of a patient's heart. The telescoping catheter delivery assembly may include an outer catheter and an inner catheter rotatable relative to and slidably received in the outer catheter. The method may also include advancing the inner catheter relative to the outer catheter to move a distal portion of the inner catheter proximate to a septal wall of the patient's heart toward a perpendicular position in the right atrium or the right ventricle relative to the septal wall. The method may further include implanting a lead and a fixation member in the septal wall through the telescoping catheter delivery assembly.

In yet another aspect, the present disclosure provides an implantable medical device including an elongate fixation member couplable to a septal wall of a patient's heart. The implantable medical device also includes an elongate lead body having a distal end portion configured to be at least partially inserted into the septal wall. The lead body is slidably coupled to and rotatable relative to the elongate fixation member. The implantable medical device also includes a plurality of electrodes. The plurality of electrodes includes a first electrode coupled to the distal end portion of the lead body implantable in the septal wall of a patient's heart to pace a first region of the patient's heart; a second electrode coupled to the lead body proximal to the first electrode to pace a second region of the patient's heart; and a third electrode coupled to the lead body proximal to the second electrode. The implantable medical device further includes a therapy delivery circuit operably coupled to the plurality of electrodes to deliver cardiac therapy to the patient's heart; a sensing circuit operably coupled to the plurality of electrodes to sense electrical activity of the patient's heart; and a controller having processing circuitry operably coupled to the therapy delivery circuit and the sensing circuit. The controller is configured to deliver cardiac therapy to the patient's heart using one or both of the first region and the second region.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
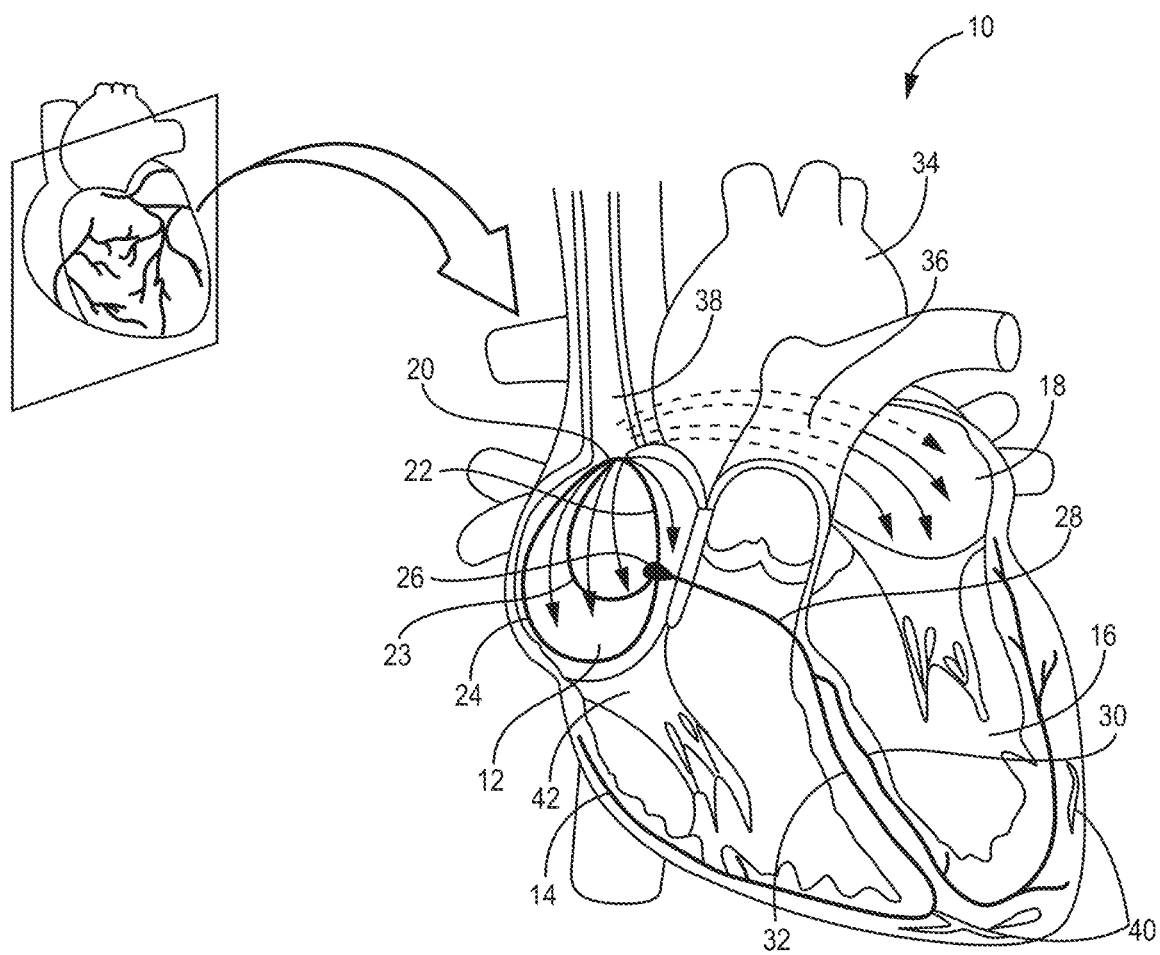
FIG. 1 is a conceptual diagram that illustrates a patient's heart as one example of an environment for using the implantable lead systems and methods of the present disclosure.

The techniques of this disclosure generally relate to implantable lead systems including adjustable fixation lead assemblies for cardiac therapy and telescoping catheter delivery assemblies for septal wall implantation. Adjustable fixation lead assemblies may include a fixation member slidably coupled to a lead. Adjustable fixation lead assemblies may facilitate implantation of the lead to an appropriate depth in a septal wall of a patient's heart. The lead may include multiple electrodes. Multiple electrodes may facilitate pacing of more than one region of the patient's heart. Lead assemblies may be delivered to the septal wall using telescoping catheter delivery assemblies. Telescoping catheter delivery assemblies may include an outer catheter and an inner catheter each including a curved region. Telescoping catheter delivery assemblies may facilitate perpendicular positioning of the lead into the septal wall.

Peri-left bundle branch pacing and AV pacing may enable physiological pacing to restore the cardiac conduction system. Some leads do not specifically address anatomical variation in human patients. A multiple-electrode lead assembly with an adjustable fixation may help to address anatomical variations during implantation. Such a lead assembly may include multiple electrodes, an adjustable fixation member, and a guide or mapping wire. The lead assembly can be delivered by a telescoping catheter system. The lead assembly can be coupled a right high septal wall or right atrium and the multiple electrode lead can penetrate into the left ventricular high septal wall or atrioventricular wall for peri-right and left bundle branch pacing or ventricle-from-atrium (VfA) AV pacing. The lead assembly may be used to deliver various types of cardiac therapy, including bradycardia therapy and cardiac resynchronization therapy. The lead assembly may include a quadripolar lead and an adjustable fixation member.

Multiple-electrode lead assemblies may be used to position electrodes to provide a pacing vector from a distal electrode positioned beyond the LBB to a proximal electrode positioned at the RBB or right atrial surface. Multiple-electrode lead assemblies may also be used to position electrodes to provide a pacing vector from one or more electrodes to a reference electrode, such as an RV lead ring electrode, an RV coil electrode, or a housing-based electrode. Such pacing vectors may facilitate pacing and sensing between electrodes for LBB pacing, bi-bundle branch pacing, AV pacing sequentially.

An implantable lead system may include an adjustable lead assembly. The lead assembly may include a fixation member and an implantable lead slidably coupled to and rotatable relative to the fixation member. The implantable lead system may include a telescoping delivery system. The delivery system may include an outer catheter and an inner catheter slidably coupled to and rotatable relative to the outer catheter. The lead assembly may be implanted in a cardiac septal wall through the delivery assembly.

Figure 2:
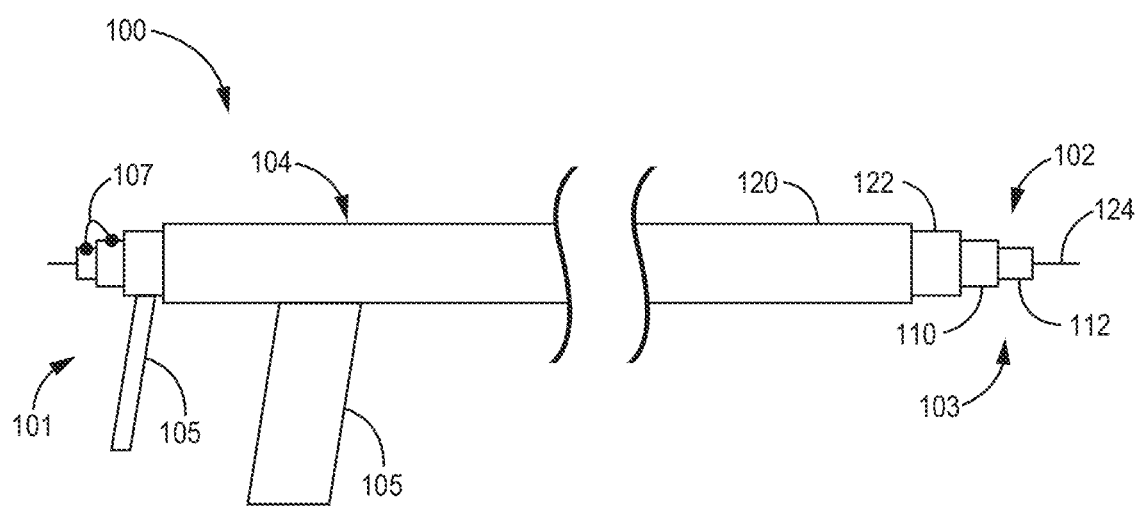
FIG. 2 is a block diagram that illustrates an implantable lead system including an adjustable fixation lead assembly and a telescoping catheter delivery assembly usable in the environment of FIG. 1.

FIG. 2 shows one example of an implantable lead system 100 including an adjustable fixation lead assembly 102 and a telescoping catheter delivery assembly 104, which may be used with the patient's heart 10 (FIG. 1). The delivery assembly 104 may slidably receive the lead assembly 102. The lead assembly 102 may be received within a lumen of the delivery assembly 104. The lead assembly 102 may extend through the delivery assembly 104. The lead assembly 102 may have a length greater than a length of the delivery assembly 104. The lead assembly 102 may concurrently extend through the proximal portion and the distal portion of the delivery assembly 104. In some embodiments, the lead assembly 102 is rotatable relative to the delivery assembly 104. In general, the delivery assembly 104 is configured to direct the lead assembly 102 to a septal wall of the patient's heart 10. The lead assembly 102 may then be implanted in the septal wall.

The implantable lead system 100 and one or more its components may extend from a proximal portion 101 to a distal portion 103. As used herein, "proximal portion" may be used interchangeably with "proximal end portion," and "distal portion" may be used interchangeably with "distal end portion," unless the context indicates otherwise. In general, a component extending from a proximal portion to a distal portion may itself also include a proximal portion and a distal portion. A proximal portion may include a proximal end. A distal portion may include a distal end.

The lead assembly 102 may be used to position one or more electrodes in a septal wall, such as an atrioventricular septal wall (AV septal wall) between the RA and LV or a ventricular septal wall (VV septal wall) between the RV and LV, at an appropriate depth. The appropriate depth may differ depending on the particular anatomy of the patient's heart 10. The delivery assembly 104 may be used to deliver the lead assembly 102 to one of the septal walls. In some embodiments, the delivery assembly 104 may position the lead assembly 102 proximate to a septal wall of the patient's heart toward a perpendicular position relative to the septal wall.

In some embodiments, the lead assembly 102 may be configured to be implanted in the AV septal wall from the RA to the LV of the patient's heart 10. The delivery assembly 104 may correspond and be configured to position the lead assembly 102 proximate to the AV septal wall in the RA.

In some other embodiments, the lead assembly 102 may be configured to be implanted in the VV septal wall from the RV to the LV of the patient's heart 10. The delivery assembly 104 may correspond and be configured to position the lead assembly 102 proximate to the VV septal wall in the RV.

As illustrated, the lead assembly 102 may include an elongate fixation member 110 and an implantable lead 112. The fixation member 110 may include a proximal portion, a distal portion, and an elongate body extending between the proximal portion and the distal portion. The elongate body of the fixation member 110 may define a lumen. The lead 112 may include a proximal portion, a distal portion, and an elongate lead body extending between the proximal portion and distal portion. The lead body of the lead 112 may define a lumen. In some embodiments, one or both of the elongate bodies of the fixation member 110 and lead 112 define a tube or tubular structure.

In general, the lead 112 may move freely relative to the fixation member 110. The free movement and telescoping relationship between the lead and the fixation member 110 may accommodate various septal wall thicknesses. The fixation member 110 may also remain fixed while the lead 112 move to different depths to facilitate securing the entry position of the lead into the septal wall.

The fixation member 110 may slidably receive the lead 112. The lead 112 may be slidably received in the lumen of the fixation member 110. The lead 112 may extend through the fixation member 110. The lead 112 may have a length greater than a length of the fixation member 110. The lead 112 may concurrently extend through the proximal portion and the distal portion of the fixation member 110. In some embodiments, the lumen of the fixation member 110 may receive the lead 112. The distal portion of the lead 112 may be configured to be at least partially inserted into the septal wall of the patient's heart 10.

The fixation member 110 may be couplable to a septal wall of the patient's heart 10. The elongate body may be formed of any suitable material configured to transfer torque from the proximal portion to the distal portion. The material may also be configured to facilitate extraction, or retraction, of the fixation member 110. Non-limiting examples of materials that may be used to form a tubular structure of the fixation member 110 include polyurethane, silicone, polyethylene, polyimide or thermoplastic elastomers or their copolymer.

In some embodiments, the lead 112 is rotatable relative to the fixation member 110. The fixation member 110 may be attached to the septal wall by screwing in a clockwise or counterclockwise motion. The lead 112 may be inserted into the septal wall by screwing in a clockwise or counterclockwise motion independent from the rotation of the fixation member 110.

The lead 112 may be implanted in the septal wall after the fixation member 110 is implanted in the septal wall. When implanted, the lead 112 may extend distally from the distal portion, or a distal end, of the fixation member 110 into the septal wall.

The lead 112 may have any suitable outer diameter. In some embodiments, the lead 112 may have an outer diameter greater than or equal to 3, 4, or 5 French. In some embodiments, the lead 112 may have an outer diameter less than or equal to 5, 4, or 3 French. In one or more embodiments, the lead 112 has an outer diameter greater than or equal to 3 French and less than or equal to 5 French.

The lead 112 may have any suitable length. In some embodiments, the lead 112 has a length greater than or equal to 55, 65, or 75 cm. In some embodiments, the lead has a length less than or equal to 88, 78, or 68 cm. In one or more embodiments, the lead 112 has a length greater than or equal to 55 cm and less than or equal to 88 cm.

The fixation member 110 may have any suitable outer diameter. In general, the outer diameter of the fixation member 110 is greater than the outer diameter of the lead 112. In some embodiments, the fixation member 110 has an outer diameter greater than or equal to 5, 6, or 7 French. In some embodiments, the fixation member 110 has an outer diameter less than 8, 7, or 6 French. In one or more embodiments, the fixation member 110 has an outer diameter greater than or equal to 5 French and less than or equal to 8 French.

The fixation member 110 may have any suitable length. In some embodiments, the fixation member 110 has a length greater than 45, 55, or 65 cm. In some embodiments, the fixation member 110 has a length less than or equal to 70, 60, or 50 cm. In one or more embodiments, the fixation member 110 has a length greater than or equal to 45 cm and less than or equal to 70 cm.

The delivery assembly 104 may be configured to telescope to accommodate various heart anatomies and sizes. Also, as can be seen in the illustrated embodiment, the delivery assembly 104 may include an outer catheter 120, an inner catheter 122, and a guide wire 124. The outer catheter 120 may include a proximal portion, a distal portion, and an elongate body extending between the proximal portion and the distal portion. The elongate body of the outer catheter 120 may define a lumen. The inner catheter 122 may include a proximal portion, a distal portion, and an elongate body extending between the proximal portion and distal portion. The elongate body of the inner catheter 122 may define a lumen. In some embodiments, one or both of the elongate bodies of the outer catheter 120 and the catheter 122 define a tube or tubular structure.

In general, the outer catheter 120 may be used to provide backup support and angular direction. The inner catheter 122 may telescope relative to the outer catheter 120 to accommodate various heart chamber sizes. The inner catheter 122 may be angled, or curved, to facilitate a perpendicular approach to the septal wall.

The outer catheter 120 and the inner catheter 122 may be formed of any suitable material. In general, one or both of the outer catheter 120 and the inner catheter 122 may be formed of an electrically insulative material. In some embodiments, one or both of the outer catheter 120 and the inner catheter 122 are formed of a semi-rigid or semi-flexible material. In general, a suitable material may be capable of holding a preformed shape in the absence of external forces and capable of flexing in response to sufficient lateral forces. For example, the material may allow the catheter to confirm to the shape of a blood vessel while advancing therethrough while reverting to the preformed shape when advanced into a chamber of the patient's heart 10.

The inner catheter 122 may be slidably received within the outer catheter 120. The inner catheter 122 may be received within the lumen of the outer catheter 120. The inner catheter 122 may extend through the outer catheter 120. The inner catheter 122 may have a length greater than a length of the outer catheter 120. The inner catheter 122 may concurrently extend through the proximal portion and the distal portion of the outer catheter 120.

In some embodiments, the inner catheter 122 is rotatable relative to the outer catheter 120. The inner catheter 122 may be manipulated to point toward the septal wall, for example, when the distal portion of the outer catheter 120 is positioned in the appropriate chamber of the patient's heart 10.

The tip of the inner catheter 122 may be configured to not penetrate tissue of the patient's heart 10. The distal portion of the inner catheter 122 may include a non-penetrating tip. The tip of the inner catheter 122 may be described as soft.

The inner catheter 122 may receive the lead assembly 102. For example, the fixation member 110 may be received within the lumen of the inner catheter 122. The fixation member 110 may extend through the inner catheter 122. The fixation member 110 may have a length greater than a length of the inner catheter 122. The fixation member 110 may concurrently extend through the proximal portion and the distal portion of the inner catheter 122.

During delivery, the lead assembly 102 may be slidably received within the inner catheter 122 and may extend distally from the distal end of the outer catheter 120 to engage the septal wall. The delivery assembly 104 may be retracted and removed proximally from the lead assembly 102, for example, after delivery, or implantation.

The guide wire 124 may be slidably received within the lead 112. A temporary pacing and sensing may be used with the guide wire 124. The lumen of the lead 112 may receive the guide wire 124. The guide wire 124 may extend through the lead 112. The guide wire 124 may have a length greater than a length of the lead 112. The guide wire 124 may concurrently extend through the proximal portion and the distal portion of the lead 112. The guide wire 124 may include a penetrating tip.

Any suitable dimensions for the guide wire 124 may be used. In some embodiments, the guide wire 124 may have a thickness or diameter greater than or equal to 0.012, 0.014, or 0.018 inches. In some embodiments, the guide wire 124 may have a thickness or diameter less than or equal to 0.035, 0.018, or 0.014 inches. In some embodiments, the guide wire 124 has a thickness or diameter greater than or equal to 0.012 inches and less than or equal to 0.035 inches.

During delivery, or implantation, the guide wire 124 may extend distally from the distal end of the lead 112 into the septal wall. The guide wire 124 may be retracted and removed proximally from the lead assembly 102, for example, after delivery, or implantation.

The guide wire 124 may include a conductor or be formed of a conductive material. Some or all of the guide wire 124 may be coated in an electrically insulative material. Non-limiting examples of electrically insulative material include polyamide and polytetrafluoroethylene (PTFE). Some or all of the guide wire 124 may be coated in a conductive material. A non-limiting example of a conductive material includes titanium nitride (TiN). In some embodiments, the guide wire 124 may include a proximal portion, a distal portion, or tip, including a coating of conductive material, and an elongate body extending between the proximal portion and the distal portion including a coating of electrically insulative material. The proximal portion, or tip, may be uncoated. In some embodiments, the guide wire 124 may be used for electrical mapping during delivery of the lead assembly 102. The guide wire 124 may be operably coupled to an analyzer.

The delivery assembly 104 may include one or more handles 105. One or both of the outer catheter 120 and the inner catheter 122 may be coupled to handles 105. The handles 105 may facilitate precise manipulation or manual operation of the catheters. The handles 105 may extend generally perpendicularly to a longitudinal direction of the elongate delivery assembly 104.

In some embodiments, the lead assembly 102 may include a securing member 107. The securing member 107 may be coupled between the fixation member 110 and the lead 112, for example, after implantation, to mitigate inner migration. For example, the securing member 107 may be coupled to the proximal portion of the lead body of the lead 112 and the proximal portion of the elongate body of the fixation member 110. Non-limiting examples of structures that may be used for the securing member 107 include one or more of the following: a suture, a clamp, a clip, or an equivalent thereof.

In the illustrated embodiment, the implantable lead system 100 includes the lead assembly 102 slidably received within the delivery assembly 104. The lead assembly 102 includes the lead 112 slidably received within the fixation member 110. The lead assembly 102 includes the securing member 107 coupled to the lead 112 and the fixation member 110 when implanted. The delivery assembly 104 includes the inner catheter 122 slidably received within the outer catheter 120. The delivery assembly 104 also includes the guide wire 124 slidably received within the lead 112. The delivery assembly 104 also includes a handle 105 coupled to each of the outer catheter 120 and the inner catheter 122. The delivery assembly 104 may be retracted from the lead assembly 102 after implantation of the lead assembly and removed from the patient's heart 10. One or both of the outer catheter 120 and the inner catheter 122 may be configured to be slit or peeled.

Figure 3:
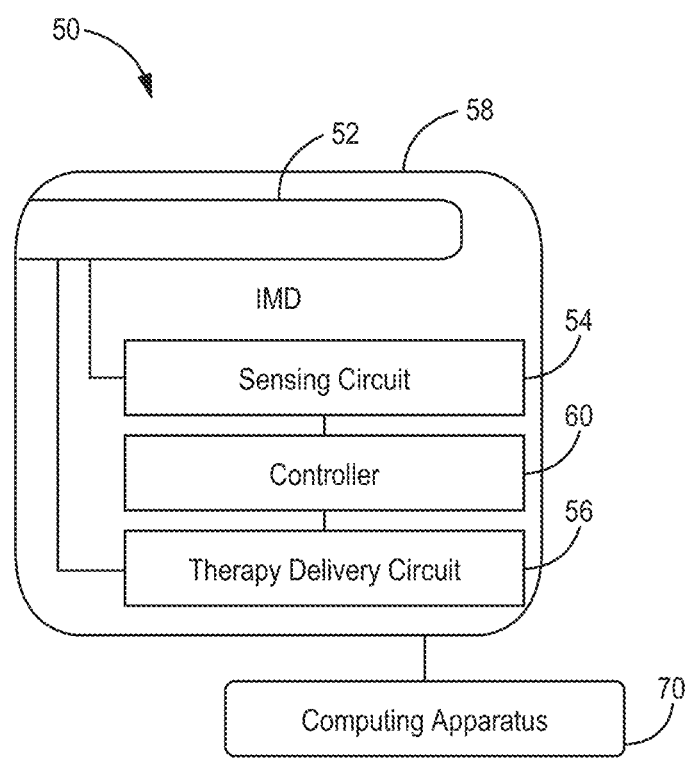
FIG. 3 is conceptual diagram that illustrates an implantable medical device and computing apparatus usable with the lead assembly of FIG. 2.

FIG. 3 is block diagram that illustrates an implantable medical device (IMD) 50 usable with the lead assembly 102 (FIG. 2). The IMD 50 includes one or more components contained within an implantable housing 58. In some embodiments, IMD 50 may be described as including the lead 112 (FIG. 2) when coupled. The IMD 50 may be any suitable type of IMD. Non-limiting examples of suitable IMDs include an implantable transvenous pacemaker, a transvenous cardiac resynchronization therapy (CRT) device, a transvenous CRT pacemaker (CRT-P), a transvenous CRT defibrillator (CRT-D), an implantable transvenous cardioverter defibrillator (ICD), a subcutaneous ICD (S-ICD), and a subcutaneous medical device.

The IMD 50 may include a connector receptacle 52 configured to receive the lead 112 or a lead connector, a sensing circuit 54 operably coupled to the connector receptacle, a therapy delivery circuit 56 operably coupled to the connector receptacle, and a controller 60 operably coupled to the therapy delivery circuit and the sensing circuit. The lead 112 may be electrically coupled to one or more of the sensing circuit 54, the therapy delivery circuit 56, and the controller 60 through the connector receptacle 52.

The therapy delivery circuit 56 is configured to deliver cardiac therapy to the patient's heart through one or more operably connected electrodes, for example, electrically connected via the connector receptacle 52. The sensing circuit 54 is configured to sense electrical activity of the patient's heart using one or more operably connected electrodes, for example electrically connected via the connector receptacle 52. The electrodes operably coupled to the sensing circuit 54 may or may not include some or all of the electrodes that are also operably coupled to the therapy delivery circuit 56. The sensing circuit 54 may monitor electrical activity of the patient's heart, for example, using electrical signals, such as electrocardiogram (ECG) signals or electrogram (EGM) signals.

The IMD 50 may be operably coupled to computing apparatus 70. The IMD 50 may be directly or indirectly coupled to the computer apparatus 70. Indirect coupling may include a network or one or more other devices. In some embodiments, the IMD 50 may be coupled by wire or wirelessly coupled to the computing apparatus 70.

The computing apparatus 70 may include a display apparatus configured to display and analyze data such as, e.g., electrical signals (e.g., electrogram data), cardiac information representative of at least one electrical cardiac functionality, mechanical cardiac functionality, etc. Cardiac information may include electrical activity data generated using electrical signals gathered, monitored, or collected, using one or more electrodes coupled to or included with the IMD 50. In at least one embodiment, the computing apparatus 70 may be a server, a personal computer, or a tablet computer. The computing apparatus 70 may be configured to receive input and transmit output, for example, to a display apparatus. Further, the computing apparatus 70 may include data storage that may allow for access to processing programs or routines and/or one or more other types of data, e.g., for driving a graphical user interface (GUI) configured to assist a user in targeting placement of a pacing device and/or evaluating pacing therapy at that location (e.g., the location of an implantable electrode used for pacing, the location of pacing therapy delivered by a particular pacing vector, etc.).

The controller 60 may have processing circuitry operably coupled to the sensing circuit 54 and the therapy delivery circuit 56. The controller 60 may be used to carry out various functionality of the IMD 50 coupled to the lead 112 or lead assembly 102. In some embodiments, the controller 60 is configured to deliver cardiac therapy to the patient's heart 10.

Processing circuitry may include any one or more of a microprocessor, a controller, a digital signal processor (DSP), an application specific integrated circuit (ASIC), a field-programmable gate array (FPGA), or equivalent discrete or integrated logic circuitry. In some examples, processing circuitry may include multiple components, such as any combination of one or more microprocessors, one or more controllers, one or more DSPs, one or more ASICs, or one or more FPGAs, as well as other discrete or integrated logic circuitry. The functions attributed to the processing circuitry of the controller herein may be embodied as software, firmware, hardware or any combination thereof. The controller may control the therapy delivery circuit to deliver stimulation therapy to the patient's heart according to a selected one or more of therapy programs, which may be stored in a memory. Specifically, the controller may control the therapy delivery circuit to deliver electrical pulses with amplitudes, pulse widths, frequency, or electrode polarities specified by the selected one or more therapy programs.

The controller 60 may include memory. Non-limiting examples of memory may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Figure 4:
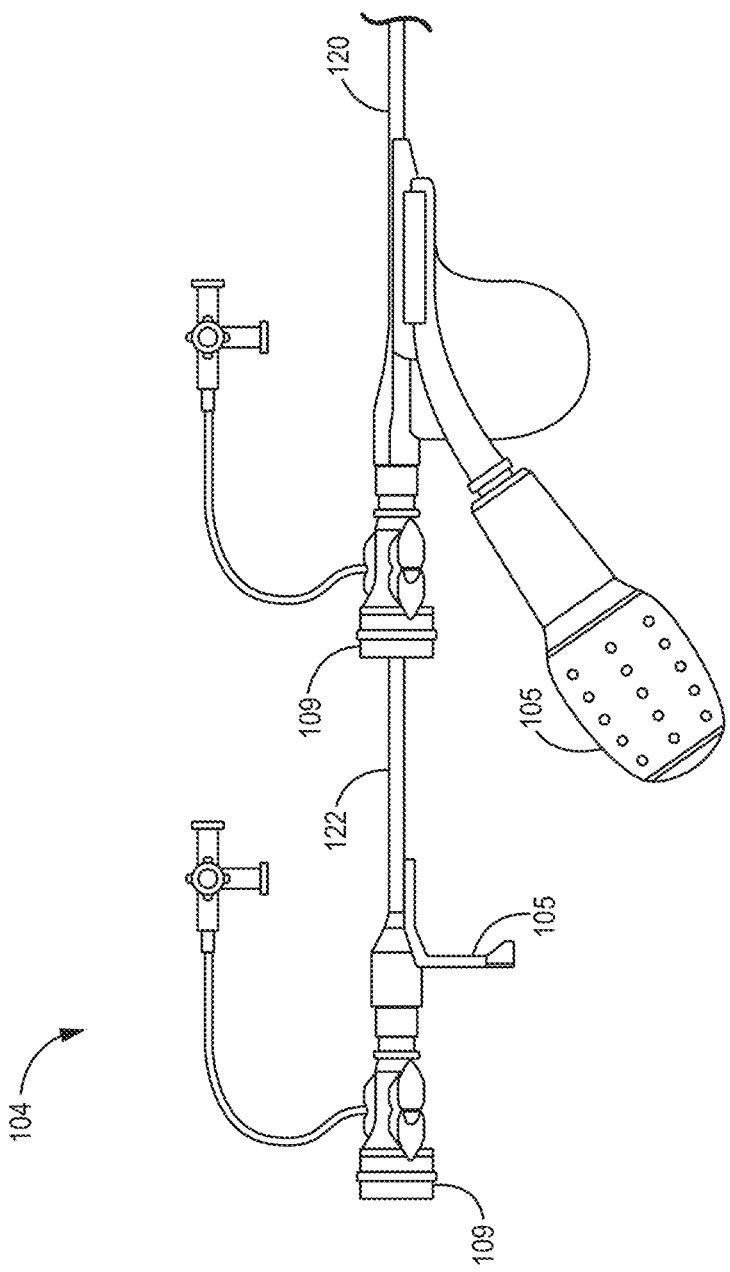
FIG. 4 is a conceptual diagram that illustrates one example of a proximal portion of the delivery assembly of FIG. 2.
Figure 5:
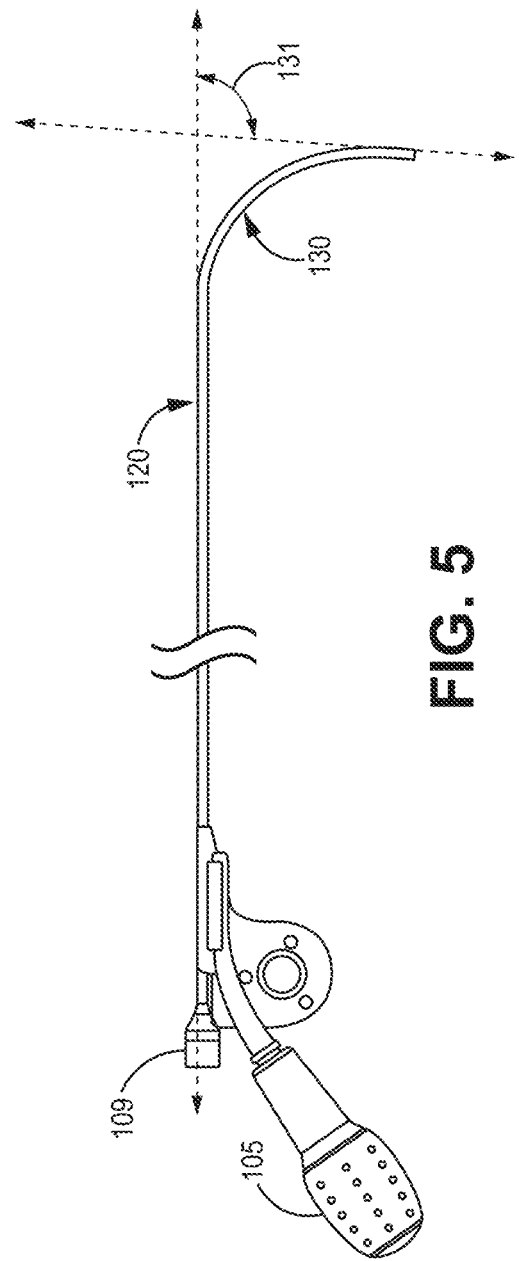
FIG. 5 is a conceptual diagram that illustrates one example of an outer catheter assembly having a curved region usable in the delivery assembly of FIG. 2.
Figure 6:
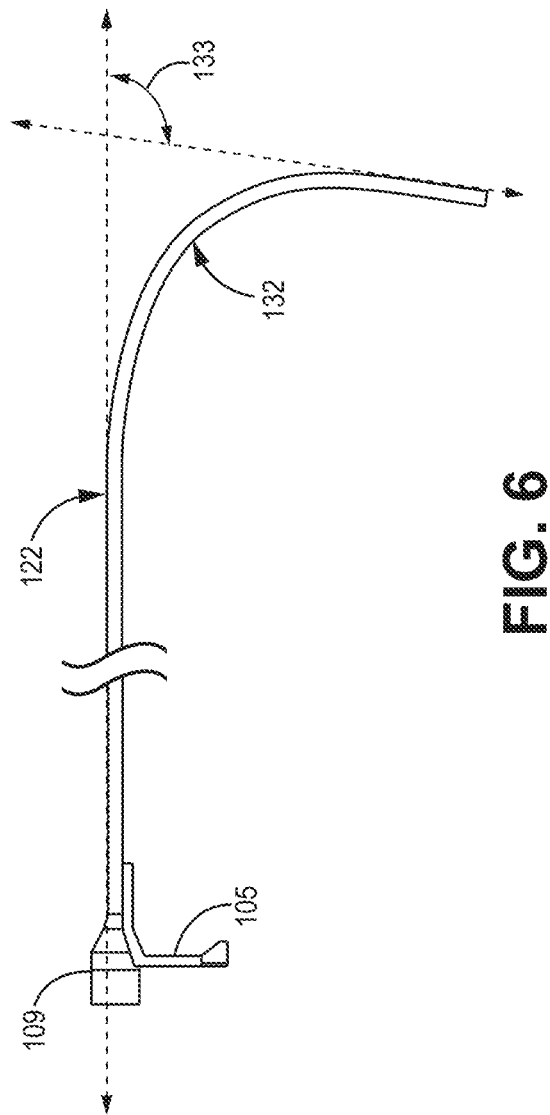
FIG. 6 is a conceptual diagram that illustrates one example of an inner catheter assembly having a curved region usable in the delivery assembly of FIG. 2.

FIGS. 4-6 show various views of one example of the delivery assembly 104 (FIG. 2). FIG. 4 shows the proximal portion of the delivery assembly 104. FIG. 5 shows the outer catheter 120. FIG. 6 shows the inner catheter 122.

As illustrated, the delivery assembly 104 includes a handle 105 coupled to each of the outer catheter 120 and the inner catheter 122. The delivery assembly 104 may include one or more valves and associated side ports positioned between the catheters 120, 122. The valves and side ports may limit blood outflow while providing access to inner lumens of the catheters 120, 122. The delivery assembly 104 may include a hub 109 coupled to each of the catheters 120, 122. The delivery assembly 104 may include a catheter slitter.

Each of the catheters 120, 122 may define a total length and a usable length. The total length of each catheter 120, 122 may be defined between the proximal end and the distal end and include portions coupled to a handle 105 or a hub 109. The usable length of each catheter 120, 122 may be defined between a portion distal to both the handle 105 and the hub 109 and the distal end. The usable length may define the length of the catheter 120, 122 that may be inserted into an incision in the patient.

The catheters 120, 122 may be preshaped to define a curve. One or both of the catheters 120, 122 may include a curved region. The outer catheter 120 includes a curved region 130. The inner catheter 122 includes a curved region 132. One or both of the catheters 120, 122 may include straight portion or linear portions proximal to the curved regions 130, 132.

In general, the outer catheter 120 including the curved region 130 is configured to position the distal portion of the outer catheter in the RA 12 or RV 14 of the patient's heart 10 when inserted from an incision in the patient's left or right pectoral through the SVC 38 (FIG. 1). The curved region 130 of the outer catheter 120 may be deflected, for example, by rotating the handle 105 coupled to the outer catheter to move the distal portion through the vasculature and into the patient's heart 10.

Figure 7:
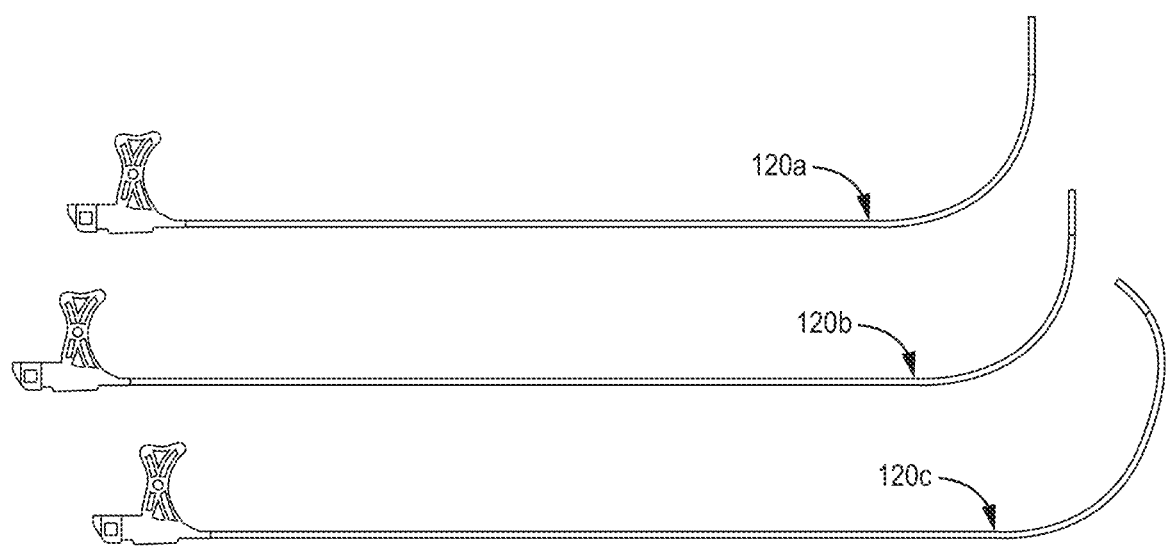
FIG. 7 is an image that illustrates various examples of an outer catheter assembly having curved regions usable in the delivery assembly of FIG. 2.

Different lengths, curvatures, or both lengths and curvatures to define the outer catheter 120 may be used depending on whether the incision is made in the patient's left or right pectoral and depending on the particular anatomy of the patient. The outer catheter 120 may have characteristics that are the same or similar to commercially available catheters. Non-limiting examples of such catheters include Model 6250V-MB2 and Model 6250V-MP from Medtronic plc of Dublin, Ireland. Such catheters may be modified for use as outer catheter 120. FIG. 7 shows various examples of outer catheters 120a, 120b, and 120c having different curved regions and lengths.

The curved region 130 may define any suitable angle 131. In some embodiments, the angle 131 may be greater than or equal to 30, 45, 90, 105, or 120 degrees. In some embodiments, the angle 131 may be less than or equal to 150, 135, 120, 105, or 90 degrees. In one or more embodiments, the angle 131 is greater than or equal to 30 degrees and less than or equal to 150 degrees.

The outer catheter 120 may have any suitable total length. In some embodiments, the outer catheter 120 has a total length greater than or equal to 40, 45, or 50 cm. In some embodiments, the outer catheter 120 has a total length less than or equal to 60, 55, or 50 cm. In one or more embodiments, the outer catheter 120 has a total length greater than or equal to 40 cm and less than or equal to 60 cm.

The outer catheter 120 may have any suitable usable length. In some embodiments, the outer catheter 120 has a total usable length greater than or equal to 20, 20, or 40 cm. In some embodiments, the outer catheter 120 has a total usable length less than or equal to 45, 35, or 25 cm. In one or more embodiments, the outer catheter 120 has a usable length greater than or equal to 20 cm and less than or equal to 45 cm.

The inner catheter 122 including the curved region 132 is generally configured to position the distal portion of the inner catheter proximate to a septal wall in the RA 12 or RV 14 of the patient's heart 10 when the inner catheter is extending distally from the outer catheter 120. The curved region 132 of the inner catheter 122 may be deflected, for example, by rotating the handle 105 coupled to the inner catheter to move the distal portion toward a perpendicular position relative to the septal wall.

When the outer catheter 120 is configured to position the inner catheter 122 in the RA 12, the inner catheter 122 may be configured to position the distal portion of the inner catheter proximate to the AV septal wall. In some embodiments, the distal portion of the inner catheter 122 is positioned proximate to the triangle of Koch region in the RA 12 and angled toward the basal region, septal region, or basal-septal region of the LV myocardium of the patient's heart 10. In some embodiments, the distal portion of the inner catheter 122 may be angled toward the high inferior/posterior basal septal region of the LV myocardium from the triangle of Koch region.

Figure 8:
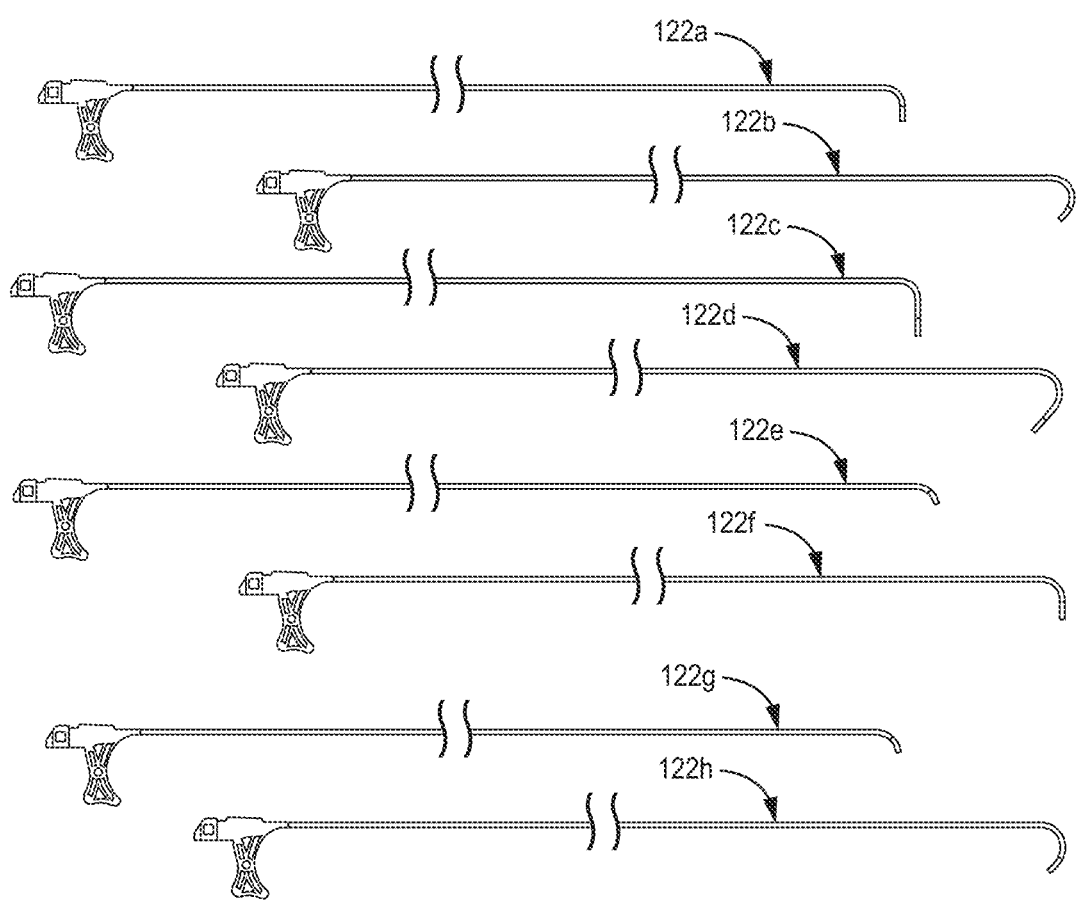
FIG. 8 is an image that illustrates various examples of an inner catheter assembly having curved regions usable in the delivery assembly of FIG. 2.

Different lengths, curvatures, or both lengths and curvatures to define the inner catheter 122 may be used depending on whether the incision is made in the patient's left or right pectoral and depending on the particular anatomy of the patient. The inner catheter 122 may have characteristics that are the same or similar to commercially available catheters. Non-limiting examples of such catheters include Model 6248V-90, Model 6248V-130, Model 6248V-90L, Model 6248V-130L, Model 6248V-90S, Model 6248V-90P (Petite), Model 6248V-90SP (Petite), and Model 6248V-130P (Petite) from Medtronic plc of Dublin, Ireland. Such catheters may be modified for use as inner catheter 122. FIG. 8 shows various examples of inner catheters 122a, 122b, 122c, 122d, 122e, 122f, 122g, and 122h having different curved regions and lengths.

The curved region 132 may define any angle 133. In some embodiments, the angle 133 may be greater than or equal to 60, 75, or 90 degrees. In some embodiments, the angle 133 may be less than or equal to 130, 110, or 90 degrees. In one or more embodiments, the curved the angle 133 is greater than or equal to 60 degrees and less than or equal to 130 degrees.

The inner catheter 122 may have any suitable total length. In some embodiments, the inner catheter 122 has a total length greater than or equal to 50, 60 or 70 cm. In some embodiments, the inner catheter 122 has a total length less than or equal to 80, 70, or 60 cm. In one or more embodiments, the inner catheter 122 has a total length greater than or equal to 50 cm and less than or equal to 80 cm.

The inner catheter 122 may have any suitable usable length. In some embodiments, the inner catheter 122 has a total usable length greater than or equal to 35, 45, or 55 cm. In some embodiments, the inner catheter 122 has a total usable length less than or equal to 65, 55, or 45 cm. In one or more embodiments, the inner catheter 122 has a usable length greater than or equal to 35 cm and less than or equal to 65 cm.

Figure 9:
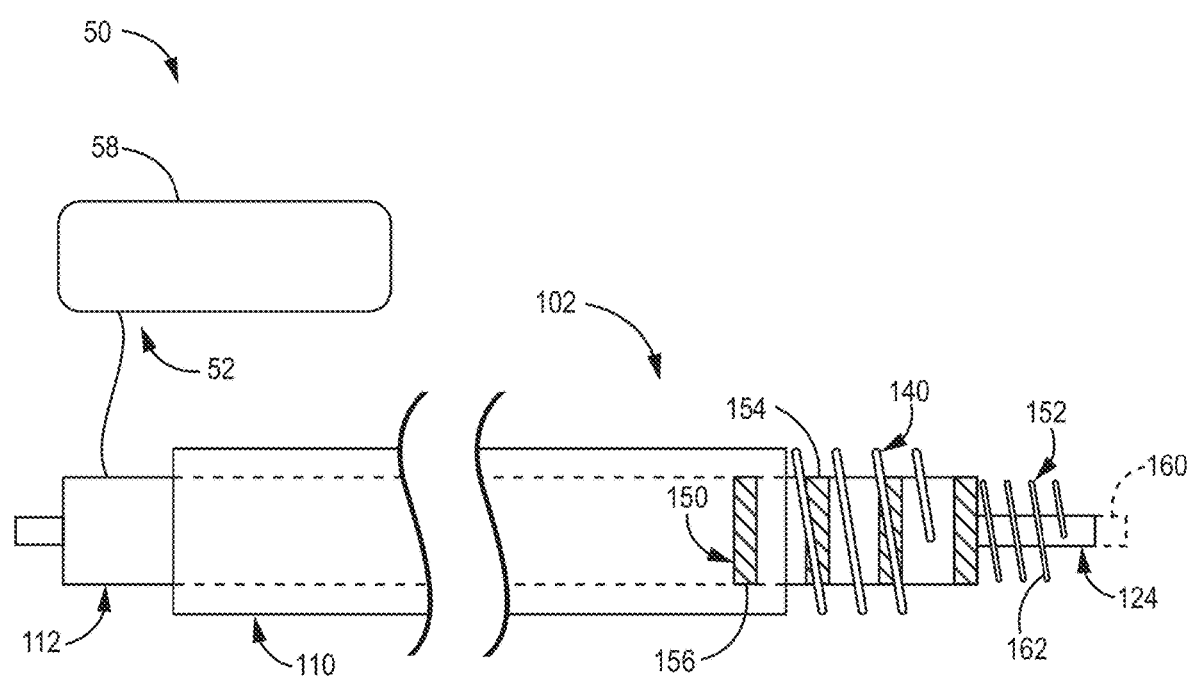
FIG. 9 is a conceptual diagram that illustrates one example of an adjustable fixation lead assembly usable in the lead assembly of FIG. 2.
Figure 10:
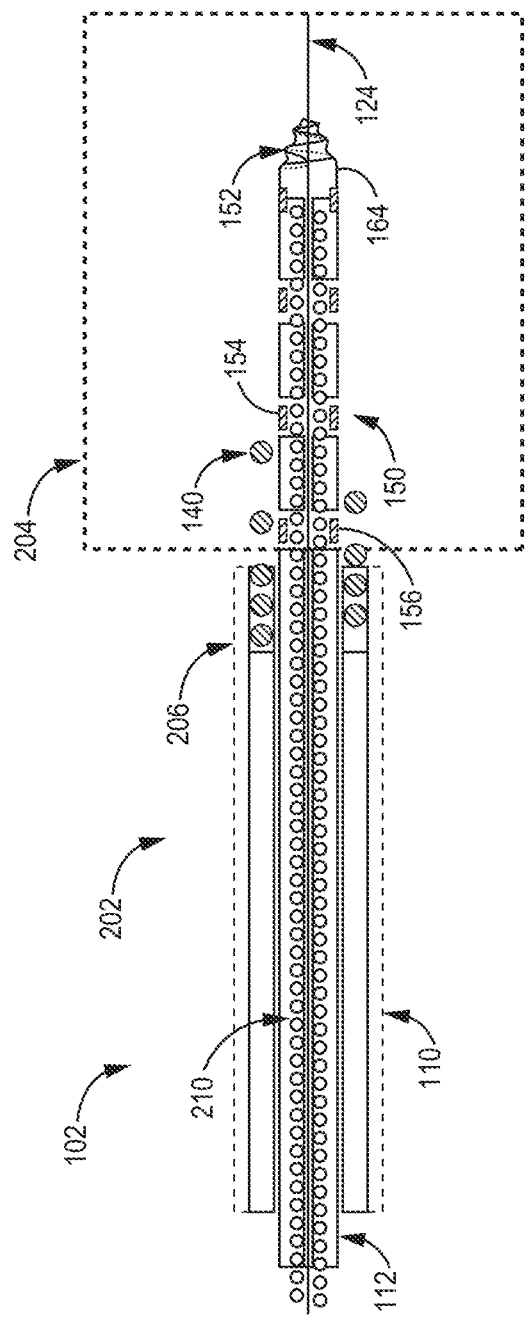
FIG. 10 is a conceptual diagram that illustrates one example of a distal portion of the lead assembly of FIG. 2.
Figure 11:
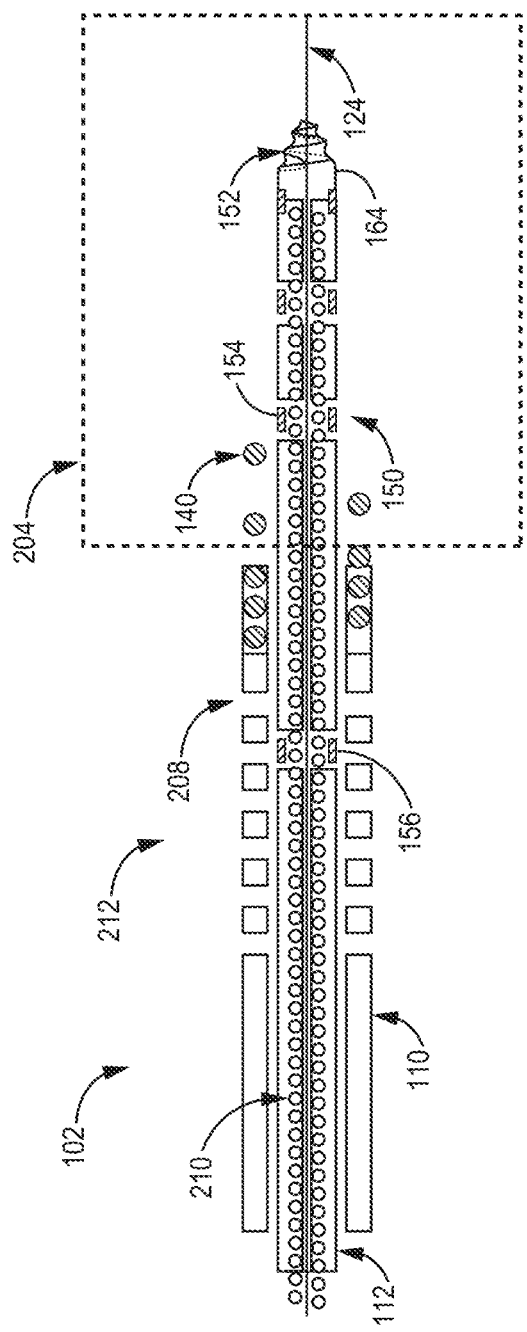
FIG. 11 is a conceptual diagram that illustrates another example of a distal portion of the lead assembly of FIG. 2.
Figure 12:
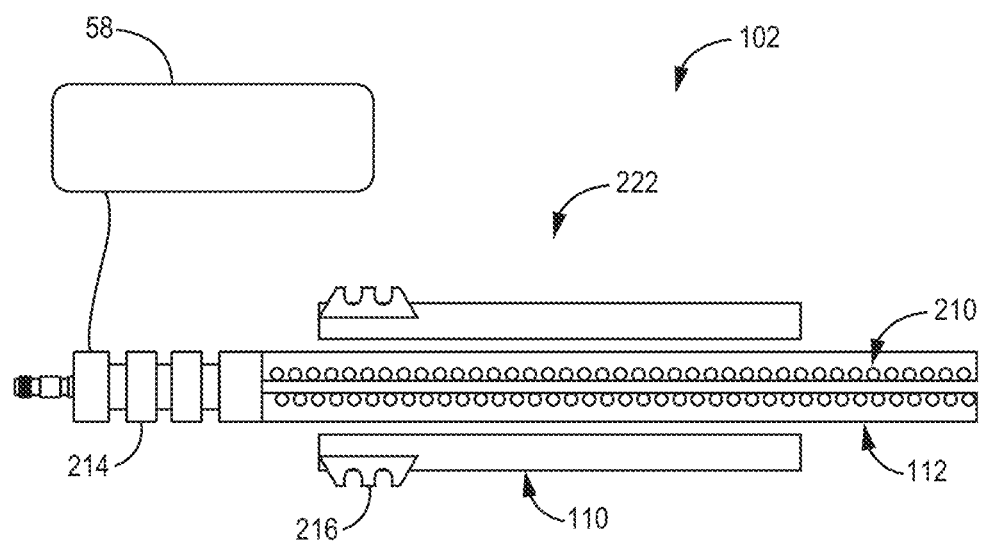
FIG. 12 is a conceptual diagram that illustrates one example of a proximal portion of the lead assembly of FIG. 2.

FIGS. 9-12 show various views of a lead assembly 102. FIG. 9 shows one example of the IMD 50 including the lead assembly 102. FIG. 10 shows one example of a distal portion 202 of the lead assembly 102. FIG. 11 shows another example of a distal portion 212 of the lead assembly 102. FIG. 12 shows one example of a proximal portion 222 of the lead assembly 102.

As can be seen in FIG. 9, the lead 442 of the lead assembly 102 may be electrically coupled to the components contained within the housing 58 through the connector receptacle 52. The lead assembly 102 may include a multipolar connector. In the illustrated embodiment of FIG. 12, the multipolar connector 214 is coupled to the lead 112. The multipolar connector 214 may be coupled, for example, to the proximal portion 222 of the lead 112. In some embodiments, the multipolar connector 214 may be a quadripolar connector. Any suitable multipolar connector 214 may be used, such as an IS4 connector.

The fixation member 110 may include a fixation element 140 coupled to a distal portion of the fixation member. The fixation element 140 may be configured to couple, or attach, to the septal wall of the patient's heart 10 (FIG. 1). Any suitable type of fixation element 140 may be used. In the illustrated embodiment, the fixation element 140 includes a helix to screw in or out of the septal wall of the patient's heart 10 in response to rotation of the fixation member 110.

In some embodiments, the fixation element 140 may be electrically conductive. The fixation element 140 may be electrically coupled to an analyzer. An electrically conductive fixation element may be used during implantation, for example, to facilitate mapping and to identify an implantation site for one or more of the electrodes.

The fixation element 140 may be electrically coupled to a proximal portion of the fixation member 110. The fixation element 140 may include a conductor extending between the distal portion and the proximal portion. In the illustrated embodiment of FIG. 10, the fixation member 110 may include an elongate braided structure 206. The elongate braided structure 206 may include a conductor electrically coupled to the fixation element 140. The conductor may be coupled to a proximal contact, such as a proximal end ring, which may be connected to an analyzer to facilitate mapping.

In some embodiments, the braided structure 206 may be formed by extruding with the tubular structure forming the fixation member 110. The braided structure 206 may also be bonded to the tubular structure. Any suitable material may be used for the braided structure 206, such as polyester or other suitable polymer. The braided structure 206 may facilitate providing torque transfer and torqueability between the proximal and distal end of the fixation member 110.

The lead 112 may include one or more electrodes. In some embodiments, the lead 112 may include a plurality of electrodes 150, or multiple electrodes, coupled to the lead body of the lead 112. For example, the lead 112 may include at least four electrodes. Each of the electrodes 150 may be independently electrically coupled to the therapy delivery circuit 56 (FIG. 3). One or more of the electrodes 150 may be implanted at an implantation site in the septal wall. In some embodiments, at least one of the electrodes 150 is not implanted in the septal wall or is positioned outside of the septal wall after implantation.

The electrodes 150 may be provided in any suitable form. For example, the electrodes 150 may be provided as ring electrodes and may include a tip electrode. The electrodes 150 may be sized and spaced, for example, to provide the functionality described herein.

In some embodiments, one or more of the electrodes 150 has a longitudinal length greater than or equal to 3, 4, or 5 mm. In some embodiments, one of more of the electrodes 150 has a longitudinal length less than or equal to 5, 4, or 3 mm. In one or more embodiments, the one or more electrodes 150 have a longitudinal length greater than or equal to 3 mm and less than or equal to 5 mm. The longitudinal length may be defined edge-to-edge.

In some embodiments, the electrodes 150 may be spaced greater than or equal to 1.3, 1.6, or 1.9 mm. In some embodiments, the electrodes 150 may be spaced less than or equal to 10, 8, 6, 4, or 2 mm. In one or more embodiments, the electrodes 150 may be spaced greater than or equal to 1.3 mm and less than or equal to 10 mm.

The distal portion of the lead 112 may include a monolithic controlled release device (MCRD). In some embodiments, one or more the electrodes 150 are associated with an MCRD. One non-limiting example of an MCRD includes a steroid. The steroid may be eluting. In some embodiments, the MCRD may be positioned on the surface of one or more of the electrodes 150. For example, an MCRD may be positioned mid-surface on an associated electrode 150. In some embodiments, MCRDs may be positioned proximate to one or more of the electrodes 150. For example, an MCRD may be positioned proximal to or distal to an associated electrode 150.

In the illustrated embodiments of FIGS. 10-12, the lead 112 may include one or more electrically insulated coil conductors 210 electrically coupled to the plurality of electrodes 150. Each of the electrodes 150 may be coupled to a different one of the coil conductors 210. For example, a different filar of the electrically insulated coil conductors 210 may be coupled to a different one of the electrodes 150. In some embodiments, the coil conductors 210 may at least partially define an inner lumen to receive the guide wire 124. As can be seen in FIG. 12, the coil conductors 210 may be electrically coupled to the multipolar connector 214. In some embodiments, the coil conductors 210 are arranged co-radially.

In the illustrated embodiment, the lead 112 includes four electrodes. In particular, the plurality of electrodes 150 includes a first electrode 152, a second electrode 154, and a third electrode 156. The first electrode 152 may be coupled to the distal portion of the lead body of the lead 112. The second electrode 154 may be coupled to the lead body of the lead 112 proximal to the first electrode 152. The third electrode 156 may be coupled to the lead body of the lead 112 proximal to the second electrode 154.

As can be seen in the illustrated embodiments of FIGS. 10-11, the first electrode 152 may be implantable in the septal wall 204 of the patient's heart 10. The first electrode 152 may pace a first region of the patient's heart 10. The second electrode 154 may be implantable in the septal wall 204 or in contact with the septal wall of the patient's heart 10. The second electrode 154 may pace a second region of the patient's heart 10. In some embodiments, a controller of the IMD 50, which may be contained within the housing 58, may be configured to deliver cardiac therapy to the patient's heart 10 using the plurality of electrodes 150. For example, the controller may be configured to deliver cardiac therapy using one or both of the first region and the second region of the patient's heart 10.

In the illustrated embodiment of FIG. 11, when the lead body of the lead 112 is implanted, the third electrode 156 may not be implanted in the septal wall 204 and electrically coupled to fluid in the patient's heart 10. The elongate body of the fixation member 110 may include a porous region 208. The porous region 208 may allow fluid communication between an outside environment and an inside environment relative to the elongate body. The porous region 208 may be configured to allow fluid communication between the third electrode 156 and fluid in the patient's heart 10. The porous region 208 may be included, for example, in at least the distal portion 212 proximate to the third electrode 156 or other electrodes 150. The porous region 208 may allow a proximal electrode under the tubular structure of the fixation member 110 to be used as a counter electrode for bipolar pacing. In some embodiments, the most proximal of the electrodes 150 may be used as the counter electrode.

The electrodes 150 may have any suitable spacing to appropriately position the electrodes for cardiac therapy. The spacing may accommodate various types of pacing, such as right-side only (such as RBB only), left-side only (such as LBB only), or multi-site (such as RBB and LBB). In some embodiments, the electrodes 150 may be evenly spaced as shown in FIG. 10. In other embodiments, the electrodes 150 may be unevenly spaced as shown in FIG. 11, wherein the third electrode 156 is spaced further from the second electrode 154 than the space between the first electrode 152 and the second electrode 154 or the space between other adjacent electrodes. In general, the electrodes 150 may be appropriately spaced for the particular type of cardiac therapy, implant location, and patient anatomy. The first electrode 152 may also be described as the distal most electrode, a distal tip electrode, or a distal end electrode.

The lead 112 may be implanted from the RA 12 to the LV 16 (FIG. 1). In some embodiments, the first region may be or include the LV myocardium of the patient's heart 10. The second region may be or include the RA myocardium of the patient's heart. In some embodiments, the first region may be or include the basal region, septal region, or basal-septal region of the LV myocardium of the patient's heart 10. In some embodiments, the first region may be or include the high inferior/posterior basal septal region of the LV myocardium. The second region may be or include the triangle of Koch region of the RA 12.

The lead 112 may be implanted from the RV 14 to the LV 16 (FIG. 1). In some embodiments, the first region may be or include the LBB 30 (FIG. 1) of the patient's heart 10. The second region may be or include the RBB 32 (FIG. 1) of the patient's heart 10.

The distal portion of the lead 112 may include a tapered or helix structure. The tapered or helix structure may include a tip electrode. In the illustrated embodiment of FIG. 9, the distal portion of the lead 112 includes a helix structure 162, and the helix structure is part of or includes the first electrode 152. In the illustrated embodiments of FIG. 11-12, the distal portion of the lead 112 includes a tapered structure 164, and the tapered structure is part of or includes the first electrode 152. Non-limiting examples of a tapered structure 164 include a bullet tip or a screw configuration.

The guide wire 124 may include a mapping electrode 160 on a distal portion of the guide wire. The guide wire 124 may be electrically coupled to an analyzer. The guide wire 124 having the mapping electrode 160 may be used during implantation, for example, to facilitate mapping and to identify an implantation site for one or more of the electrodes. Such a guide wire 124 may be described as a mapping wire or a mapping and guide wire.

The lead assembly 102 may include a lead fixation sleeve. In the illustrated embodiment of FIG. 12, a lead fixation sleeve 216 is coupled to the fixation element 110. In some embodiments, the lead fixation sleeve 216 may be included, for example, in at least the proximal portion 222 of the fixation element 110.

Figure 13:
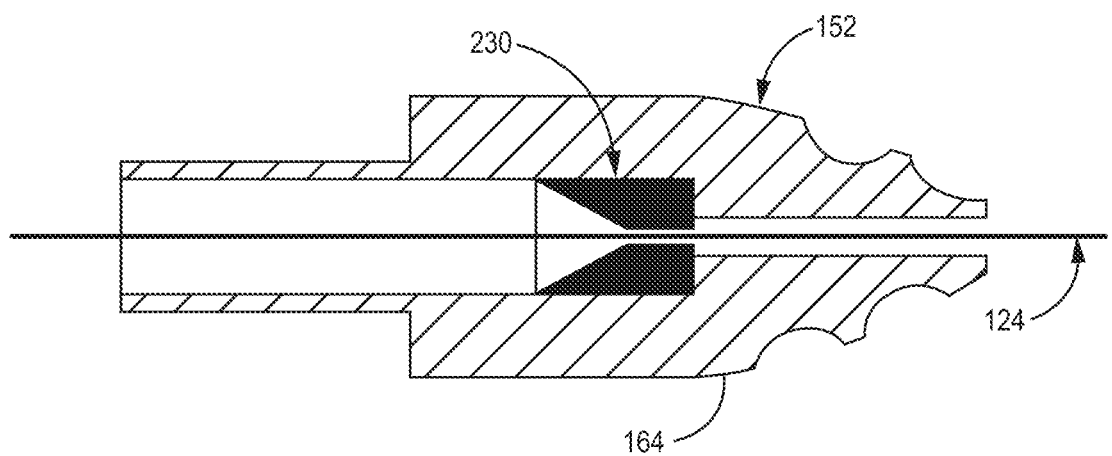
FIG. 13 is a conceptual diagram that illustrates one example of an electrode and sealing element usable in the lead assembly of FIG. 2.

FIG. 13 shows one example of the tapered structure 164 that may be used in the lead 112. The tapered structure 164 may be used as an electrode, such as the first electrode 152.

The first electrode 152 may define at least part of the inner lumen, which may be used to receive the guide wire 124. In some embodiments, the tapered structure 164 may define at least part of the inner lumen.

The lead assembly 102 may include a sealing element 230 coupled to the first electrode 152. The sealing element 230 may prevent or at least partially prevent blood ingress. The sealing element 230 may form a seal, or a partial seal, between the guide wire 124 and an inner surface of the first electrode 152. Any suitable material may be used to form the sealing element 230, such as silicone. Any suitable sealing element may be used for sealing element 230, such as those described in U.S. Pat. No. 7,386,351 (Hine et al.), granted Jun. 10, 2008, which is incorporated by reference.

The sealing element 230 may be described as a tip seal. The sealing element 230 may be positioned between any tubular structures in the implantable lead system 100 (FIG. 2). In some embodiments, one or more sealing elements 230 may be used between pairs of one or more of the following components: the outer catheter 120, inner catheter 122, fixation member 110, lead 112, and guide wire 124. In other embodiments, the sealing element 230 may be absent, and the lead assembly 102 may be described as having an open lumen design.

Figure 14:
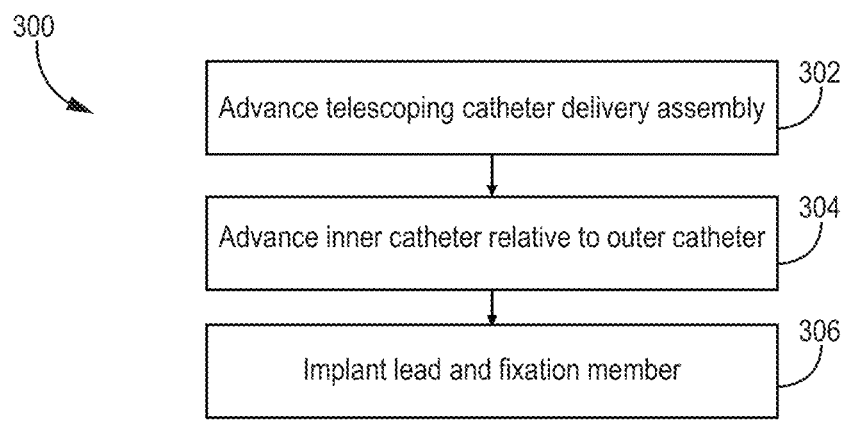
FIG. 14 is a flow diagram that illustrates a method for use with the implantable lead system of FIG. 2.

FIG. 14 shows one example of a method 300 for use with the implantable lead system 100 (FIG. 2). The method 300 may include advancing a telescoping catheter delivery assembly or system 302. The delivery assembly may be delivered into the RA 12 or RV 14 of the patient's heart 10 (FIG. 1). The delivery assembly may include an outer catheter and an inner catheter rotatable relative to and slidably received in the outer catheter.

The method 300 may include advancing the inner catheter relative to the outer catheter 304. The inner catheter may be moved by manual operation, or manipulation, of the inner catheter relative to the outer catheter. Advancement of the inner catheter may move a distal portion of the inner catheter proximate to a septal wall of the patient's heart 10. The distal portion of the inner catheter may be moved toward a perpendicular position in the RA 12 or RV 14 relative to the septal wall.

The method 300 may also include implanting a lead and fixation member 306. The lead and fixation member may be implanted in the septal wall through the telescoping catheter delivery assembly. The lead may be rotatable relative to and slidably received in the fixation member. The lead may be insertable at different depths within the septal wall when the fixation member is fixed to the septal wall.

The method 300 may also include advancing a guide wire through the lead before implantation is complete. The guide wire may be used to test potential implantation sites at different depths of the guide wire in the septal wall. Determining whether any of the potential implantation sites is acceptable may be based on the testing. In response to identifying that none of the potential implantation sites is acceptable, the guide wire may be retracted. The telescoping catheter delivery assembly may be manipulated to a different position or angle relative to the septal wall. In response to identifying that at least one of the potential implantation sites is acceptable, the lead may be advanced into the septal wall. One or more depths of the lead may be tested. An acceptable implantation site may be identified based on the testing.

The method 300 may also include slitting or peeling the telescoping catheter delivery assembly after implantation of the lead is complete.

In some embodiments, the method 300 may also include delivering cardiac therapy using one or more electrodes of the lead. Different electrodes may be implanted at different depths within the septal wall. In some embodiments, electrical activity may be sensed in or cardiac therapy may be delivered to one or both of the RA myocardium and the LV myocardium. In some embodiments, the lead may be positioned to sense electrical activity or deliver cardiac therapy to the basal region, septal region, or basal-septal region of the LV myocardium. In other embodiments, electrical activity may be sensed in or cardiac therapy may be delivered to the bundle branch conduction system including one or both of the LBB and the RBB.

Figure 15:
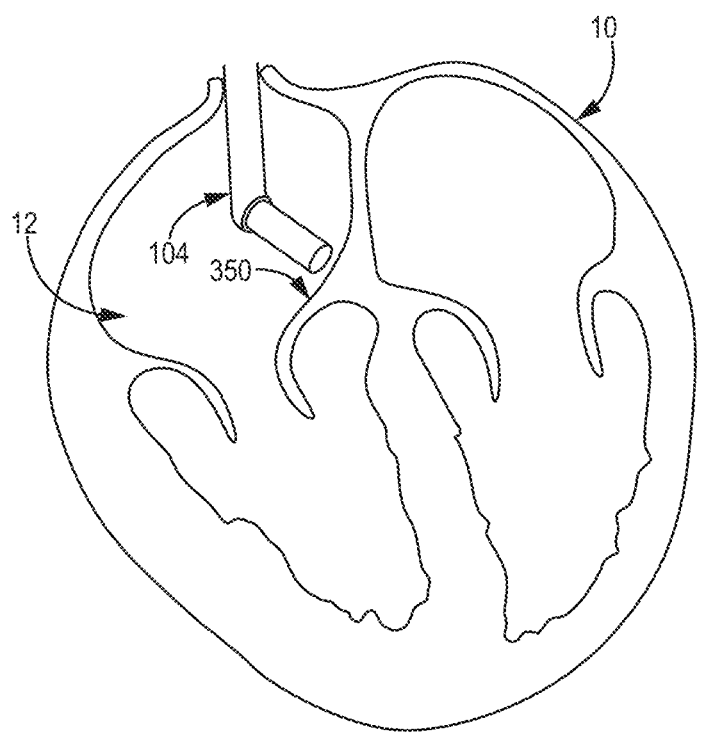
FIGS. 15-17 are conceptual diagrams that illustrate various stages of implantation in the atrioventricular septal wall using the implantable lead system of FIG. 2.
Figure 16:
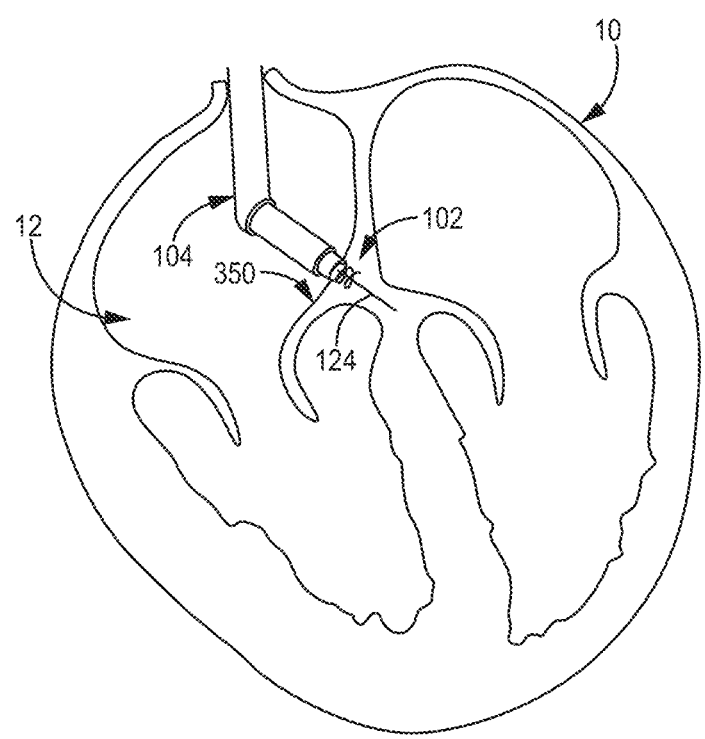
Figure 17:
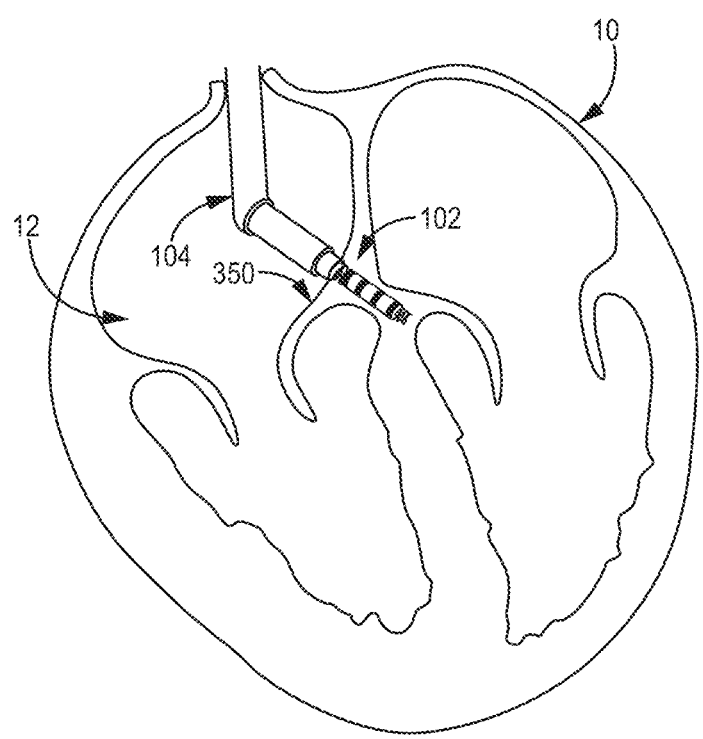

FIGS. 15-17 show various stages of implantation in the AV septal wall using the implantable lead system 102 (FIG. 2). FIG. 15 shows the telescoping catheter delivery assembly 104 inserted into the RA 12 of the patient's heart 10. The inner catheter extends past a distal end of the outer catheter. The distal portion of the inner catheter is positioned in a perpendicular position to a surface of the AV septal wall 350.

FIG. 16 shows the adjustable fixation lead assembly 102 guided by the delivery assembly 104 and fixed to the AV septal wall 350. The guide wire 124 is inserted into the AV septal wall 350. The guide wire 124 may be a mapping guide wire used to test potential implantation sites at different depths within the AV septal wall 350.

FIG. 17 shows the lead assembly 102 implanted at an implantation site in the AV septal wall 350. One or more electrodes may be used to deliver cardiac therapy using one, two, or more regions of the patient's heart 10.

Figure 18:
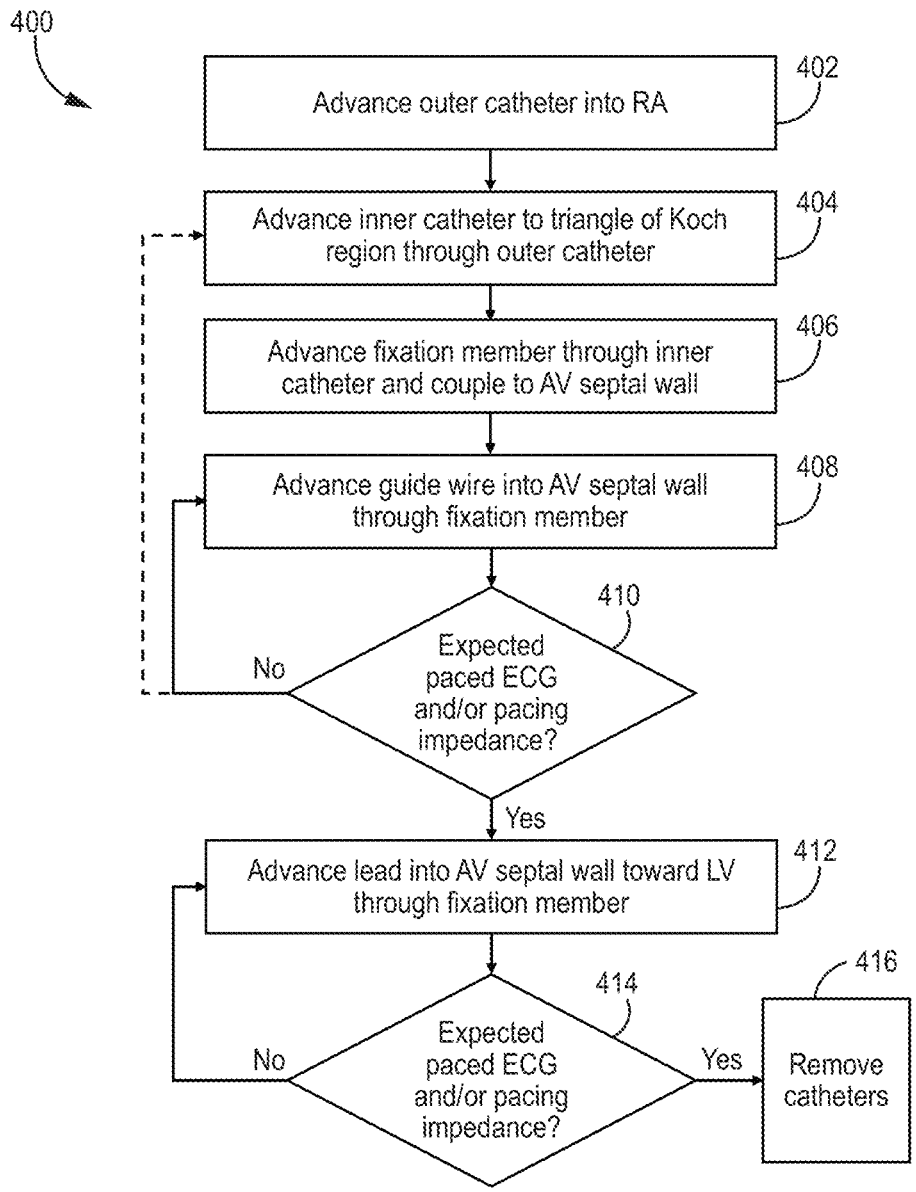
FIG. 18 is a flow diagram that illustrates a method of implantation in the atrioventricular septal wall using the implantable lead system of FIG. 2.

FIG. 18 shows a method 400 of implantation in the AV septal wall using the implantable lead system 100 (FIG. 2). The method 400 may include advancing an outer catheter into the RA 402. The outer catheter may be guided through an incision in a left or right pectoral and guided through the SVC to the RA.

Advancing an inner catheter to the triangle of Koch region through the outer catheter 404 may be included in the method 400. The triangle of Koch region may form at least part of the surface of the AV septal wall. Advancing the inner catheter may include pushing and rotating the inner catheter to position a distal end of the inner catheter perpendicular to the triangle of Koch region.

Advancing a fixation member through the inner catheter and coupling the fixation member to the AV septal wall 406 may be included in the method 400. The fixation member may include a fixation element. The fixation member may be rotatable to screw the fixation element into the AV septal wall.

Advancing a guide wire into the AV septal wall through the fixation member 408 may be included in the method 400. The guide wire may be an active mapping wire.

Determining whether an expected paced ECG and/or pacing impedance is detected 410 may be included in the method 400. The guide wire may be used to electrically test various depths within the AV septal wall. Detecting the expected paced ECG and/or pacing impedance may indicate that the depth of the guide wire is associated with a target implantation site in the AV septal wall. The ECG may be detected using any suitable ECG device or system.

In response to not detecting the expected paced ECG and/or pacing impedance, the method 400 may reposition the guide wire 408 and perform further testing 410. In some embodiments, in response to not detecting the expected paced ECG and/or pacing impedance, the method 400 may retract the guide wire and fixation member and reposition the inner catheter to a new location in the AV septal wall 404. For example, if all depths tested by the guide wire do not result in an expected paced ECG and/or pacing impedance, another location of the AV septal wall may be tested by repositioning the inner catheter, fixation member, and guide wire.

The method 400 may include advancing a lead into the AV septal wall toward the LV through the fixation member 412, for example, in response to detecting the expected paced ECG and/or pacing impedance. In some embodiments, the lead may be advanced through the triangle of Koch region in the RA. A positive detection by the guide wire may indicate that a target implantation site is reachable at the current location of the fixation member. The guide wire may be retracted and removed before or after advancing the lead.

Determining whether an expected paced ECG and/or pacing impedance is detected 414 may be included in the method 400. One or more electrodes of the lead may be used to electrically test various depths within the AV septal wall. In response to not detecting the expected paced ECG and/or pacing impedance, the method 400 may continue to advance the lead further into the AV septal wall 412. In some embodiments, the lead may be advanced by rotating the lead in a first direction and may be retracted by rotating the lead in a second opposite direction.

The method 400 may include removing the catheters of the delivery assembly 416. The lead may be coupled to electronics in a housing of an IMD. The implantation of the lead may be considered complete.

Figure 19:
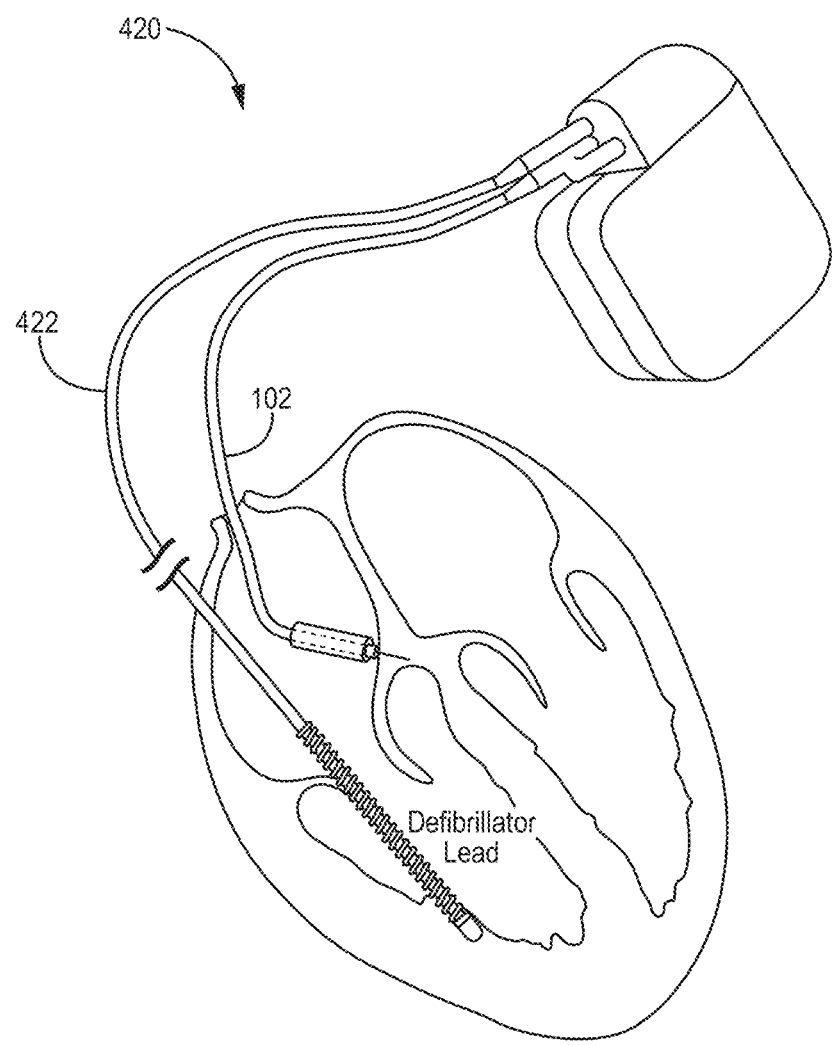
FIG. 19 is a conceptual diagram of an implantable medical device including the lead assembly of FIG. 2 implanted in the atrioventricular septal wall.

FIG. 19 shows one example of an IMD 420 including the lead assembly 102 implanted in the AV septal wall. The lead assembly 102 may be used to provide VfA pacing (e.g., DDDR-type pacing). The defibrillator lead 422 may be implanted, for example, in the RV of the patient's heart. The defibrillator lead 422 may be used to provide defibrillation to the patient's heart.

Figure 20:
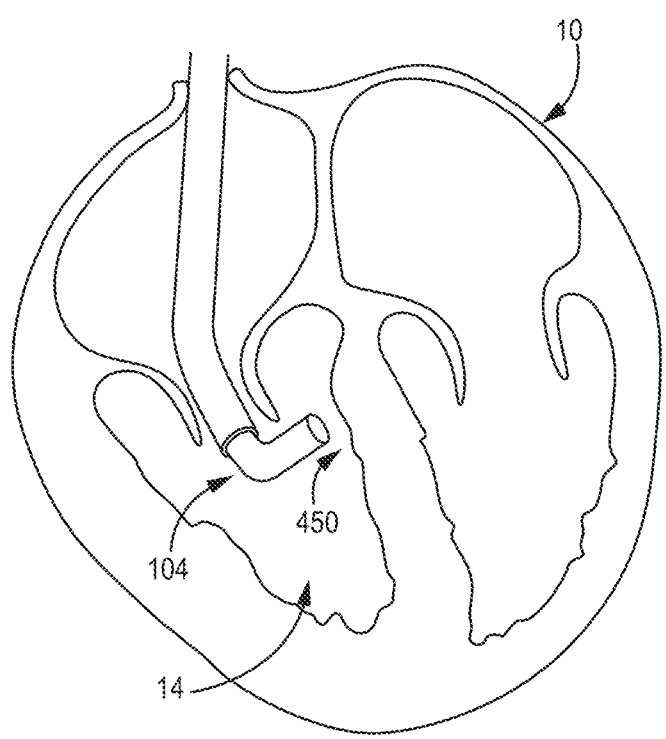
FIGS. 20-22 are conceptual diagrams that illustrate various stages of implantation in the ventricular septal wall using the implantable lead system of FIG. 2.
Figure 21:
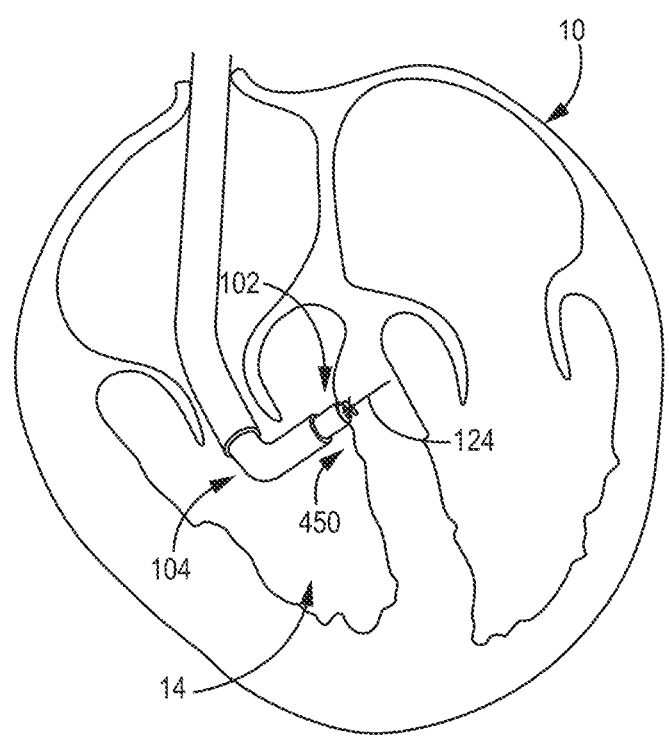
Figure 22:
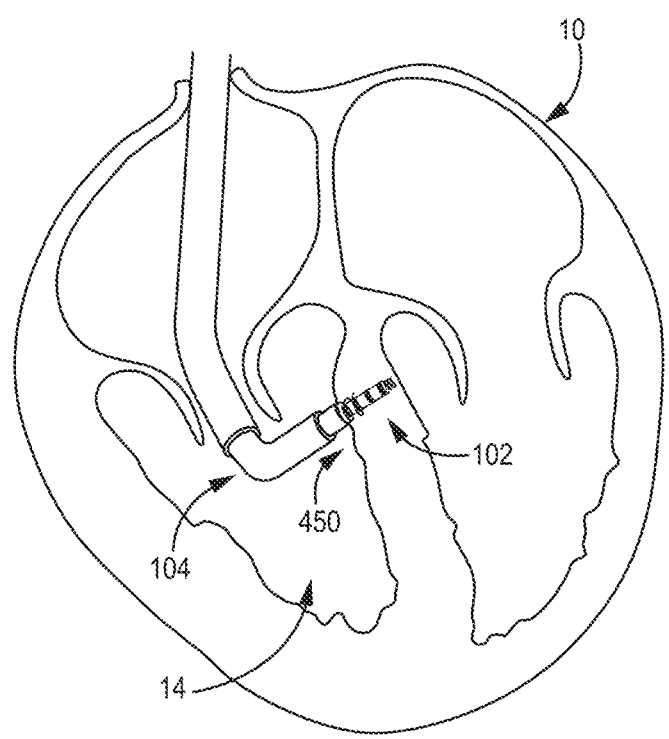

FIGS. 20-22 show various stages of implantation in the VV septal wall using the implantable lead system 102 (FIG. 2). FIG. 20 shows the telescoping catheter delivery assembly 104 inserted into the RV 14 of the patient's heart 10. The inner catheter extends past a distal end of the outer catheter. The distal portion of the inner catheter is positioned in a perpendicular position to a surface of the VV septal wall 450.

FIG. 21 shows the adjustable fixation lead assembly 102 guided by the delivery assembly 104 and fixed to the VV septal wall 450. The guide wire 124 is inserted into the VV septal wall 450. The guide wire 124 may be a mapping guide wire used to test potential implantation sites at different depths within the VV septal wall 450.

FIG. 22 shows the lead assembly 102 implanted at an implantation site in the VV septal wall 450. One or more electrodes may be used to deliver cardiac therapy using one, two, or more regions of the patient's heart 10.

Figure 23:
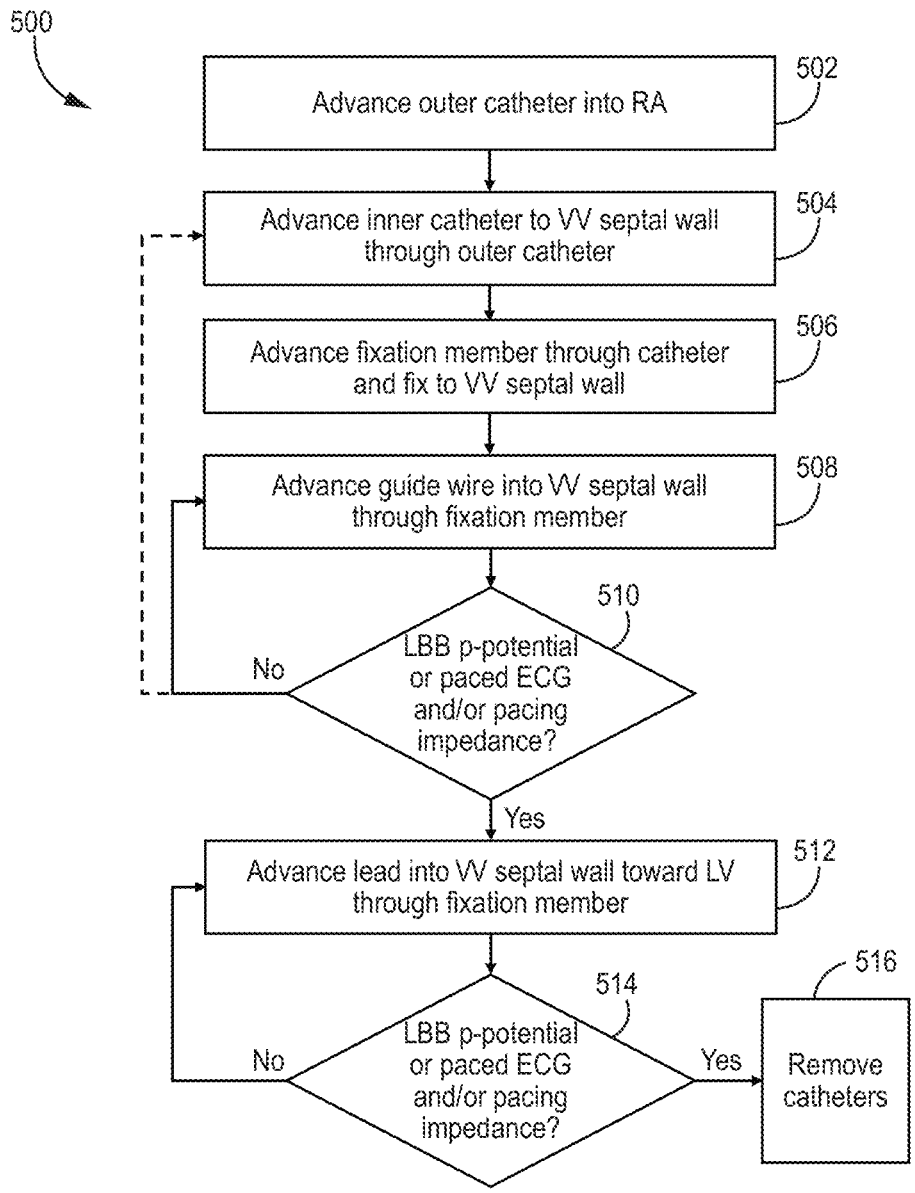
FIG. 23 is a flow diagram that illustrates a method of implantation in the ventricular septal wall using the implantable lead system of FIG. 2.

FIG. 23 shows a method 500 of implantation in the VV septal wall using the implantable lead system 100 (FIG. 2). The method 500 may include advancing an outer catheter into the RV 502. The outer catheter may be guided through an incision in a left or right pectoral and guided through the SVC and tricuspid valve to the RV.

Advancing an inner catheter to the VV septal wall through the outer catheter 504 may be included in the method 500. Advancing the inner catheter may include pushing and rotating the inner catheter to position a distal end of the inner catheter perpendicular to the VV septal wall.

Advancing a fixation member through the inner catheter and coupling the fixation member to the AV septal wall 506 may be included in the method 500. The fixation member may include a fixation element. The fixation member may be rotatable to screw the fixation element into the VV septal wall.

Advancing a guide wire into the AV septal wall through the fixation member 508 may be included in the method 500. The guide wire may be an active mapping wire.

Determining whether an LBB p-potential, expected paced ECG, and/or pacing impedance is detected 510 may be included in the method 500. The guide wire may be used to electrically test various depths within the VV septal wall. Detecting the LBB p-potential, expected paced ECG, and/or pacing impedance may indicate that the depth of the guide wire is associated with a target implantation site in the VV septal wall. The ECG may be detected using any suitable ECG device or system. The LBB p-potential may be detected using the guidewire electrode EGM.

In response to not detecting the LBB p-potential, expected paced ECG, and/or pacing impedance, the method 500 may reposition the guide wire 508 and perform further testing 510. In some embodiments, in response to not detecting the LBB p-potential, expected paced ECG, and/or pacing impedance, the method 500 may retract the guide wire and fixation member and reposition the inner catheter to a new location in the VV septal wall 504. For example, if all depths tested by the guide wire do not result in an expected paced ECG and/or pacing impedance, another location of the AV septal wall may be tested by repositioning the inner catheter, fixation member, and guide wire.

The method 500 may include advancing a lead into the VV septal wall toward the LV through the fixation member 512, for example, in response to detecting the LBB p-potential, expected paced ECG, and/or pacing impedance. A positive detection by the guide wire may indicate that a target implantation site is reachable at the current location of the fixation member. The guide wire may be retracted and removed before or after advancing the lead.

Determining whether an LBB p-potential, expected paced ECG, and/or pacing impedance is detected 514 may be included in the method 500. One or more electrodes of the lead may be used to electrically test various depths within the VV septal wall. In response to not detecting the LBB p-potential, expected paced ECG, and/or pacing impedance, the method 500 may continue to advance the lead further into the VV septal wall. In some embodiments, the lead may be advanced by rotating the lead in a first direction and may be retracted by rotating the lead in a second opposite direction.

The method 500 may include removing the catheters of the delivery assembly 516. The lead may be coupled to electronics in a housing of an IMD. The implantation of the lead may be considered complete.

Figure 24:
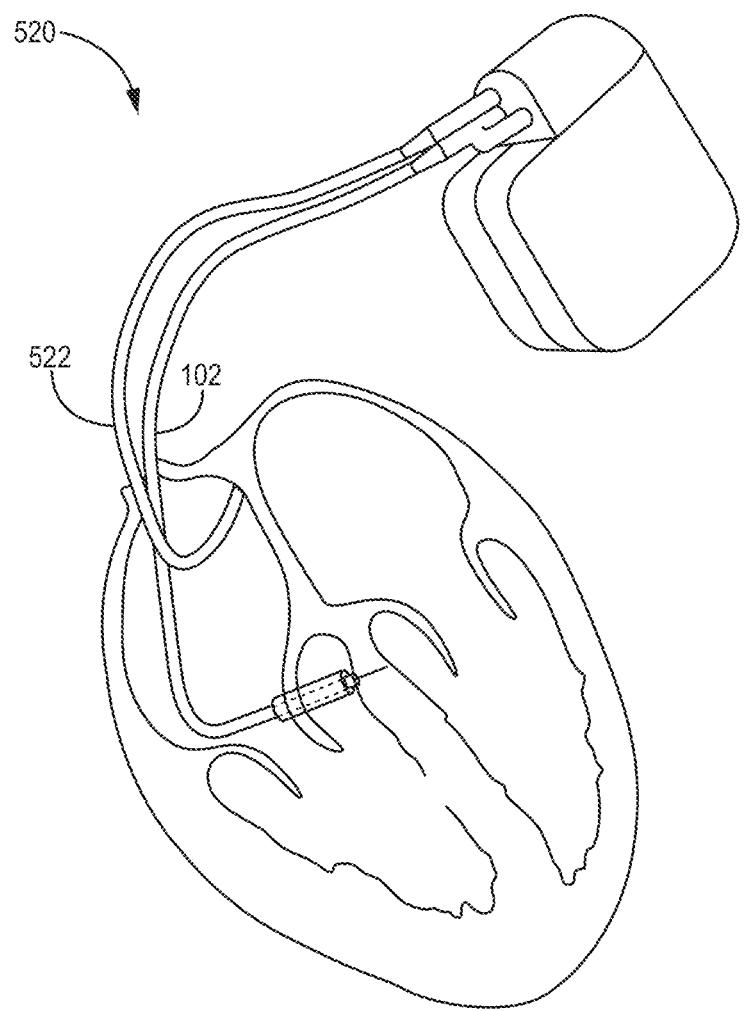
FIG. 24 is a conceptual diagram of an implantable medical device including the lead assembly of FIG. 2 implanted in the ventricular septal wall and an atrial lead.

FIG. 24 shows one example of an IMD 520 including the lead assembly 102 implanted in the VV septal wall. The lead assembly 102 may be used to provide dual bundle-branch pacing (e.g., DDDR-type pacing). The IMD 520 also includes an atrial lead 522. The atrial lead 522 may be implanted in the RA. The atrial lead 522 may sense or pace in the RA.

Figure 25:
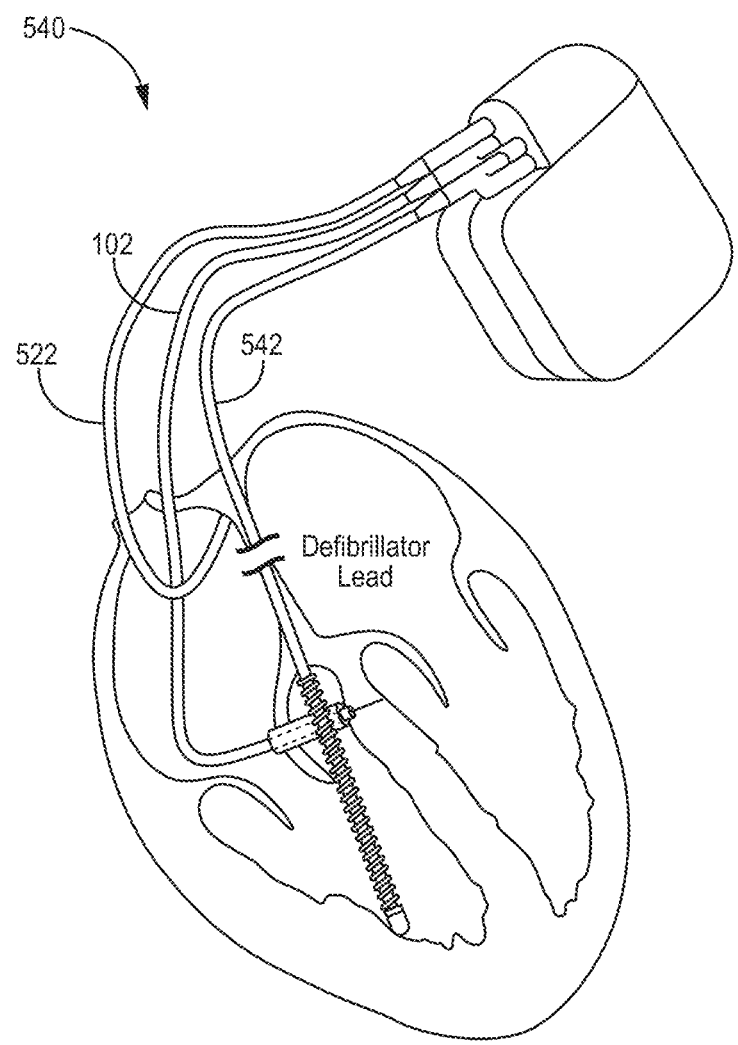
FIG. 25 is a conceptual diagram of an implantable medical device including the lead assembly of FIG. 2 implanted in the ventricular septal wall, an atrial lead, and a defibrillator lead.

FIG. 25 shows one example of an IMD 540 including the lead assembly 102 implanted in the VV septal wall. The lead assembly 102 may be used to provide dual bundle-branch pacing (e.g., biventricular pacing). The IMD 520 also includes an atrial lead 522. The atrial lead 522 may be implanted in the RA. The atrial lead 522 may sense or pace in the RA. The IMD 520 also includes a defibrillator lead 542. The defibrillator lead 542 may be implanted, for example, in the RV of the patient's heart. The defibrillator lead 542 may be used to provide defibrillation to the patient's heart.

The implantable lead system 100 (FIG. 2) may be used in conjunction with a graphical user interface (GUI) on a computing apparatus 70 (FIG. 3). A most distal electrode of the lad may be targeted for placement beneath the LBB in the VV septal wall (which may be referred to as the LV1 electrode). A most proximal electrode may be targeted for placement outside of the VV septal wall (which may be referred to as the LV4 electrode). One or more other electrodes of the lead between the most distal and most proximal electrodes may be targeted for placement in contact with the right side of the VV septal wall (which may be referred to as the LV2 and LV3 electrodes). The GUI may be used to view electrical activity to determine whether one or more of the electrodes are in the targeted locations for placement. The GUI may be also be used to program a CRT device including the lead for dual-bundle branch or bi-bundle branch pacing using, for example, a pacing vector from LV1 to LV4 and a pacing vector from LV2 or LV3 to LV4. In another example, the CRT-D device including the lead may be programmed for dual-bundle branch or bi-bundle branch pacing using, for example, a pacing vector from LV1 to an RV coil on a defibrillator lead and a pacing vector from LV2 or LV3 to the RV coil.

The implantable lead system 100 (FIG. 2) may also be used to implant the lead assembly 102 (FIG. 2) in other tissue structures of the cardiovascular system. For example, the lead assembly 102 may be implanted in the coronary sinus or coronary vein through the coronary sinus ostium using any suitable technique. Various techniques for implanting lead assemblies that may be used include any described in U.S. Pat. No. 10,315,028 (Sommer et al.), granted Jun. 11, 2019, and U.S. Pat. No. 10,092,744 (Sommer et al.), granted Oct. 9, 2018, which are incorporated by reference.

Figure 26:
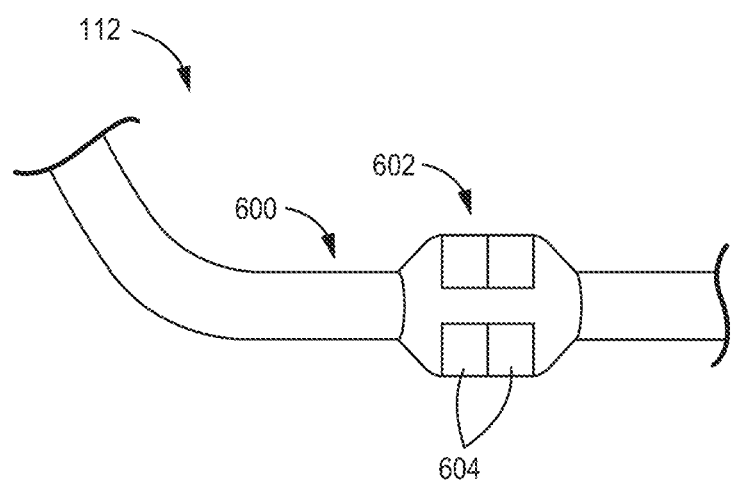
FIG. 26 is a conceptual diagram of an electrode assembly usable in the lead assembly of FIG. 2.

FIG. 26 shows one example of an electrode assembly 602 that maybe used on an implantable lead, such as the implantable lead 112. The electrode assembly 602 protrudes relative to the lead body 600 of the lead 112. More particularly, the width, or diameter, of the electrode assembly 602 is larger than the diameter of the lead body 600 such that the electrode assembly 602 protrudes relative to lead body 600. The relationship between diameter of electrode assembly 602 the diameter of the lead body 600 may aid in facilitating contact with tissue traverse, or lateral to, the lead body 600.

In some embodiments, the electrode assembly 602 may be used to control a depth of a stimulation field. The protruded electrode assembly 602 may extend the stimulation field farther from the longitudinal axis of lead body 122. In particular, the protruded electrode assembly 602 may aid in increasing the distance the stimulation field extends from an outer diameter of lead body 600 in radial direction perpendicular to the longitudinal axis of lead body relative to an electrode having a diameter equal to diameter of lead body.

A stimulation field with increased depth may be useful in delivering stimulation to a target stimulation site further from the lead body 600 than reachable if the diameter of the electrode assembly 602 equaled the diameter of the lead body.

The electrode assembly 602 may include one or more electrode segments 604. The electrode assembly 602 may be described as a segmented or partial ring electrode or electrode assembly. In the illustrated embodiment, four segments 604 are shown. In some embodiments, the segments 604 may be used to facilitate selectability of different segments 604 to pace or otherwise electrically stimulate tissue at different angles around the lead 112. For example, various segments 604 may be selectable to target a particular stimulation site traverse to the lead 112. One or more of the segments 604 may be independently operably coupled to sensing or pacing circuitry.

In some embodiments, the segments 604 may be used to steer a stimulation field. Each of the electrode segments 604 may extend along an arc less than 360 degrees, such as 90, 120, or 180 degrees. Segmented or partial ring electrodes may be useful for providing an electrical stimulation field that is predominantly focused in a particular transverse direction relative to the longitudinal axis of the lead 112. In other embodiments, instead of or in addition to the segments 604, the lead 112 may include a ring electrode extending substantially around the entire periphery, e.g., circumference, of the lead body.

The segments 604, but need not be, located at the same axial position along the length of the lead body 600. When the segments 604 are located at the same axial position of lead body 600, the segments 604 may form a row of electrode segments. In some embodiments, segments 604 may be evenly spaced around the periphery of the lead 112. Additionally, each of individual electrode segments 604 may be separated by insulative material, which may aid in electrically isolating each of the segments 604.

Each of the segments 604 can be made from an electrically conductive, biocompatible material, such as platinum iridium. In addition, at least one of the segments 604 may function as a sensing electrode that monitors internal, physiological, electrical signals of the patient or a pacing electrode that provides electrical pulses to patient tissue.

Within lead body 600, the lead 112 may also include insulated electrical conductors (not shown) coupled to each segment 604. Some conductors may be coiled along the length of lead body 600 (in a multiconductor coil). Other conductors may be disposed axially and may not be coiled. In some embodiments, each conductor may be electrically coupled to a single electrode segment 604. In this manner, each segment 604 may be independently activated. In other embodiments, a lead including multiple electrodes may include a multiplexer or other switching device such that the lead may include fewer conductors than electrodes, while allowing each of the electrodes to be independently activated. The switching device may be responsive to commands from processing circuitry or an external source to selectively couple the electrodes to the conductors for delivery of stimulation or for sensing.

In general, any of the electrodes used by the lead 112 may be segmented or include segments 604, such as electrodes 152, 154, 156 (see FIGS. 9-11). Various configurations for electrodes similar to the electrodes 152, 154, 156 except as segmented electrodes are shown in FIGS. 27-29.

Figure 27:
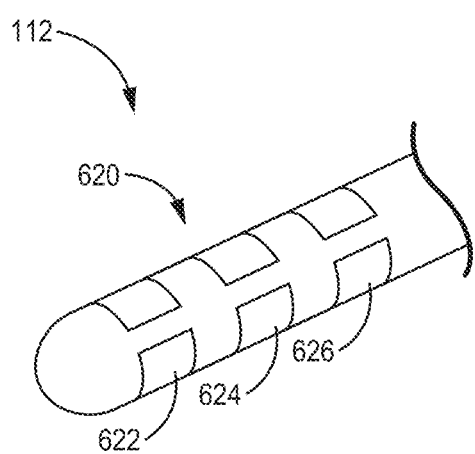
FIGS. 27-29 are conceptual diagrams of electrode arrangements usable in the lead assembly of FIG. 2.

FIG. 27 is a perspective illustration showing a first example of an electrode arrangement 620 that may be used with the lead 112. The electrode arrangement 620 may include segmented electrodes 622, 624, 626, which may be disposed axially spaced from one another along the lead 112. In the illustrated embodiment, each electrode 622, 624, 626 includes two segments. The segments of the electrodes 622, 624, 626 may be evenly spaced in an axial direction and in an angular direction around the lead 112. As shown, the electrodes 622, 624, 626 are flush or isodiametric with lead body.

Figure 28:
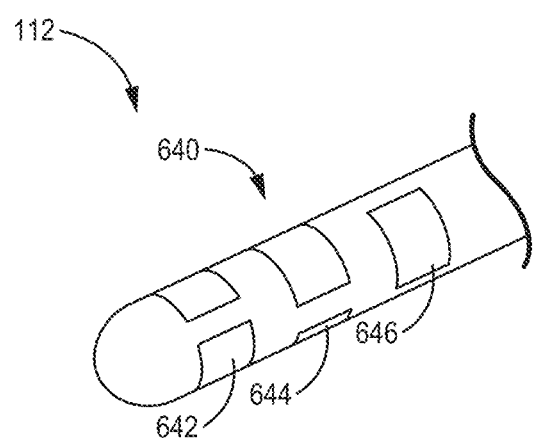

FIG. 28 is a perspective illustration showing a second example of an electrode arrangement 640 that may be used with the lead 112. The electrode arrangement 640 may include segmented electrodes 642, 644, 646, which may be disposed axially spaced from one another along the lead 112. In the illustrated embodiment, each of electrodes 642, 644 include two segments. The electrode 646 may include only one segment. The segments of the electrodes 642, 644, 646 may be evenly spaced in an axial direction. The segments of the electrodes 642, 644 may be spaced evenly in an angular direction around the lead 112. As shown, the electrodes 642, 644, 646 are flush or isodiametric with lead body.

Figure 29:
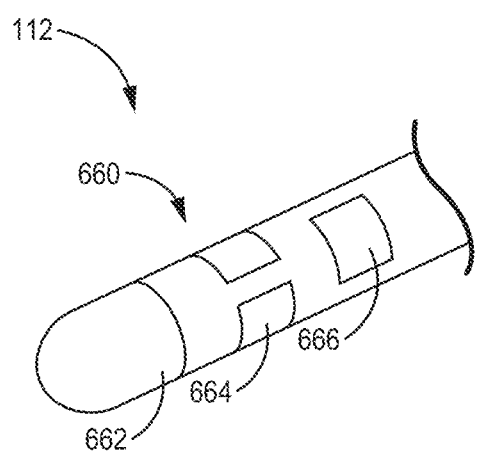

FIG. 29 is a perspective illustration showing a second example of an electrode arrangement 660 that may be used with the lead 112. The electrode arrangement 660 may include segmented electrodes 662, 664, 666, which may be disposed axially spaced from one another along the lead 112. In the illustrated embodiment, electrode 664 includes two segments. Each of electrodes 662, 666 may include only one segment. The electrode 662 may be described as a distal tip electrode. The segments of the electrodes 662, 664, 666 may be evenly spaced in an axial direction. The segments of the electrode 664 may be spaced evenly in an angular direction around the lead 112. As shown, the electrodes 662, 664, 666 are flush or isodiametric with lead body.

Illustrative Embodiments

While the present disclosure is not so limited, an appreciation of various aspects of the disclosure will be gained through a discussion of the specific illustrative embodiments provided below. Various modifications of the illustrative embodiments, as well as additional embodiments of the disclosure, will become apparent herein.

A1. An implantable lead system comprising:
a fixation member comprising a proximal portion, a distal portion, a fixation element coupled to the distal portion, and an elongate body extending between the proximal portion and the distal portion, the fixation element configured to attach to a septal wall of a patient's heart, the elongate body configured to transfer torque from the proximal portion to the distal portion; and
an implantable lead comprising a proximal portion, a distal portion, a lead body extending between the proximal portion and the distal portion, and an electrode coupled to the distal portion, the distal portion configured to be at least partially inserted into the septal wall, the electrode configured to be implanted at an implantation site in the septal wall, wherein the implantable lead is slidably coupled to and rotatable relative to the fixation member.

A2. The system according to embodiment A1, wherein the elongate body of the fixation member defines a lumen and the implantable lead is slidably received in the lumen.

A3. The system according to embodiment A1 or A2, wherein the fixation element comprises a helix to screw in or out of the septal wall in response to rotation of the fixation member.

A4. The system according to any preceding A embodiment, wherein the fixation element is electrically conductive and electrically coupled to the proximal portion of the fixation member.

A5. The system according to any preceding A embodiment, wherein the elongate body comprises a braided structure.

A6. The system according to embodiment A5, wherein the braided structure comprises a conductor electrically coupled to the fixation element.

A7. The system according to any preceding A embodiment, wherein the elongate body comprises a porous region to allow fluid communication between an outside and an inside of the elongate body.

A8. The system according to any preceding A embodiment, wherein the implantable lead comprises multiple electrodes coupled to the lead body.

A9. The system according to embodiment A8, wherein the implantable lead comprises one or more electrically insulated coil conductors electrically coupled to the multiple electrodes.

A10. The system according to embodiment A8 or A9, wherein each of the multiple electrodes are independently electrically coupled to a therapy delivery circuit of an implantable medical device.

A11. The system according to any of embodiments A8 to A10, wherein when the implantable lead is implanted, at least one of the electrodes is not implanted in the septal wall.

A12. The system according to any preceding A embodiment, wherein the implantable lead defines an inner lumen to receive a guide wire.

A13. The system according to embodiment A12, wherein the electrode of the implantable lead defines at least part of the inner lumen.

A14. The system according to embodiment A13, further comprising a sealing element coupled to the electrode of the implantable lead to form a fluid seal between the guide wire and an inner surface of the electrode.

A15. The system according to any preceding A embodiment, wherein the distal portion of the implantable lead comprises a tapered or helix structure comprising the electrode.

A16. The system according to any preceding A embodiment, further comprising a securing member to couple the proximal portion of the fixation member and the proximal portion of the implantable lead.

A17. The system according to any preceding A embodiment, further comprising telescoping delivery catheters defining catheter lumens to receive the fixation member and the implantable lead and to position the fixation member and the implantable lead proximate to the septal wall.

A18. The system according to any preceding A embodiment, wherein the electrode of the implantable lead comprises a segmented electrode including two or more segments angularly spaced from one another.

B1. A lead delivery system comprising:
an outer catheter comprising a proximal portion, a distal portion, and an elongate body extending between the proximal portion and the distal portion, the elongate body defining a lumen, wherein the elongate body defines a first curved region configured to position the distal portion of the outer catheter in the right atrium or the right ventricle of a patient's heart when the elongate body extends through the superior vena cava of the patient's heart; and
an inner catheter comprising a proximal portion, a distal portion, and an elongate body extending between the proximal portion and the distal portion, the elongate body defining a lumen, the inner catheter being receivable into the lumen of the outer catheter, wherein the inner catheter is slidably coupled to and rotatable relative to the outer catheter and wherein the elongate body of the inner catheter defines a second curved region configured to move the distal portion of the inner catheter proximate to a septal wall of the patient's heart toward a perpendicular position relative to the septal wall.

B2. The system according to embodiment B1, wherein the outer catheter is configured to be implanted from a left or right pectoral of the patient through the superior vena cava and into the right atrium or the right ventricle of the patient's heart.

B3. The system according to embodiment B1 or B2, wherein one or both of the outer catheter and the inner catheter are formed of a deflectable material.

B4. The system according to any preceding B embodiment, wherein the distal portion of the inner catheter comprises a non-penetrating tip.

B5. The system according to any preceding B embodiment, wherein the second curved region defines an angle between 60 degrees and 130 degrees.

B6. The system according to any preceding B embodiment, wherein one or both of the outer catheter and the inner catheter are coupled to a respective handle to facilitate manual operation.

B7. The system according to any preceding B embodiment, further comprising a guide wire configured to extend through the second lumen of the inner catheter.

B8. The system according to embodiment B7, wherein the guide wire comprises a conductor and is configured to be used for electrical mapping.

B9. The system according to any preceding B embodiment, wherein one or both of the outer catheter and the inner catheter are slittable or peelable.

B10. The system according to any preceding B embodiment, further comprising an implantable lead received within the lumen of the inner catheter to be implanted in the septal wall using guidance from the outer catheter and the inner catheter.

C1. A method for delivering an implantable lead system comprising:
advancing a telescoping catheter delivery assembly into to the right atrium or the right ventricle of a patient's heart, the telescoping catheter delivery assembly comprising an outer catheter and an inner catheter rotatable relative to and slidably received in the outer catheter;
advancing the inner catheter relative to the outer catheter to move a distal portion of the inner catheter proximate to a septal wall of the patient's heart toward a perpendicular position in the right atrium or the right ventricle relative to the septal wall; and
implanting a lead and a fixation member in the septal wall through the telescoping catheter delivery assembly.

C2. The method according to embodiment C1, wherein implanting the lead and the fixation member comprises implanting the lead and the fixation member in the atrio-ventricular septal wall between right atrium and the left ventricle to deliver cardiac therapy to one or both of the right atrial myocardium and the left ventricular myocardium.

C3. The method according to embodiment C2, wherein implanting the lead and the fixation member comprises implanting the lead and the fixation member through the triangle of Koch region in the right atrium of a patient's heart to deliver cardiac therapy to or sense electrical activity of the left ventricle in the basal region, septal region, or basal-septal region of the left ventricular myocardium of the patient's heart.

C4. The method according to embodiment C1, wherein implanting the lead and the fixation member comprises implanting the lead and the fixation member in the ventricular septal wall to deliver cardiac therapy to the bundle branch conduction system of the patient's heart including one or both of the left bundle branch of the patient's heart and the right bundle branch of the patient's heart.

C5. The method according to any preceding C embodiment, further comprising:
  advancing a guide wire through the lead and into the septal wall;
  testing potential implantation sites at different depths of the guide wire in the septal wall;
  determining whether any of the potential implantation sites is acceptable based on the testing; and
  in response to identifying that none of the potential implantation sites is acceptable, retracting the guide wire and manipulating the telescoping catheter delivery assembly to a different position or angle relative to the septal wall.

C6. The method according to embodiment C5, further comprising, in response to identifying that at least one of the potential implantation sites is acceptable,
  advancing the lead into the septal wall;
  testing one or more depths of the lead in the septal wall; and
  identifying an acceptable implantation site based on the testing.

C7. The method according to any preceding C embodiment, further comprising slitting or peeling the telescoping catheter delivery assembly.

C8. The method according to any preceding C embodiment, further comprising delivering cardiac therapy using one or more electrodes of the lead.

D1. An implantable medical device comprising:
  an elongate fixation member couplable to a septal wall of a patient's heart;
    an elongate lead body comprising a distal end portion configured to be at least partially inserted into the septal wall, the lead body being slidably coupled to and rotatable relative to the elongate fixation member;
  a plurality of electrodes comprising:
    a first electrode coupled to the distal end portion of the lead body implantable in the septal wall of a patient's heart to pace a first region of the patient's heart;
    a second electrode coupled to the lead body proximal to the first electrode to pace a second region of the patient's heart; and
    a third electrode coupled to the lead body proximal to the second electrode;
  a therapy delivery circuit operably coupled to the plurality of electrodes to deliver cardiac therapy to the patient's heart;
  a sensing circuit operably coupled to the plurality of electrodes to sense electrical activity of the patient's heart; and
  a controller comprising processing circuitry operably coupled to the therapy delivery circuit and the sensing circuit, the controller configured to deliver cardiac therapy to the patient's heart using one or both of the first region and the second region.

D2. The device according to embodiment D1, wherein the distal end portion of the lead body comprises a tapered or helix structure comprising the first electrode.

D3. The device according to embodiment D1 or D2, wherein when the lead body is implanted, one or both of the first electrode and the second electrode are implanted in the septal wall.

D4. The device according to any preceding D embodiment, when the lead body is implanted, the third electrode is not implanted in the septal wall and electrically coupled to fluid in the patient's heart.

D5. The device according to any preceding D embodiment, wherein the plurality of electrodes comprises at least four electrodes.

D6. The device according to any preceding D embodiment, wherein the first region comprises the left ventricular myocardium of the patient's heart and the second region comprises the right atrial myocardium of the patient's heart.

D7. The device according to embodiment D6, wherein the first region comprises the basal region, septal region, or basal-septal region of the left ventricular myocardium and the second region comprises the triangle of Koch region in the right atrium of the patient's heart.

D8. The device according to any one of embodiments D1 to D5, wherein the first region comprises the left bundle branch of the patient's heart and the second region comprises the right bundle branch of the patient's heart.

D9. The device according to any preceding D embodiment, wherein the fixation member defines a lumen and the lead body is slidably received in the lumen.

D10. The device according to any preceding D embodiment, wherein the fixation member comprises a fixation element including a helix structure to screw in or out of the septal wall in response to rotation of the fixation member.

D11. The device according to any preceding D embodiment, wherein the fixation element is electrically conductive.

D12. The device according to any preceding D embodiment, wherein the fixation member comprises an elongate braided structure.

D13. The device according to any preceding D embodiment, wherein the fixation member comprises a porous region to allow fluid communication between the third electrode and fluid in the patient's heart.

D14. The device according to any preceding D embodiment, wherein the plurality of electrodes are coupled to one or more electrically insulated coil conductors.

D15. The device according to embodiment D14, wherein the one or more electrically insulated coil conductors define an inner lumen to receive a guide wire.

D16. The device according to embodiment D14 or D15, wherein the first electrode defines at least part of the inner lumen.

D17. The device according to embodiment D15 or D16, further comprising a sealing element coupled to the first electrode of the implantable lead to form a fluid seal between the guide wire and an inner surface of the electrode.

D18. The device according to any preceding D embodiment, further comprising a securing member to couple a proximal end portion of the fixation member and a proximal end portion of the lead body.

D19. The device according to any preceding D embodiment, wherein the implantable medical device comprises one or more of the following: an transvenous implantable pacemaker, a cardiac resynchronization therapy (CRT) device, a transvenous CRT pacemaker (CRT-P), a transvenous CRT defibrillator (CRT-D), an implantable transvenous cardioverter defibrillator (ICD), a subcutaneous ICD (S-ICD), and a subcutaneous medical device.

D20. The device according to any preceding D embodiment, wherein at least one of the first electrode, the second electrode, and the third electrode comprises a segmented electrode including two or more segments angularly spaced from one another.

Thus, various embodiments of ADJUSTABLE LEAD SYSTEMS FOR CARDIAC SEPTAL WALL IMPLANTATION Adjustable lead systems for CARDIAC septal wall implantation are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

Terms related to orientation, such as "proximal," "distal," "top," "bottom," "side," and "end," are used to describe relative positions of components and are not meant to limit the absolute orientation of the embodiments contemplated.

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out functionality.

As used herein, the term "configured to" may be used interchangeably with the terms "adapted to" or "structured to" unless the content of this disclosure clearly dictates otherwise.

The term "or" is generally employed in its inclusive sense, for example, to mean "and/or" unless the context clearly dictates otherwise. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. An implantable lead system comprising:
   a fixation member comprising a proximal portion, a distal portion, a fixation element coupled to the distal portion, and an elongate body extending between the proximal portion and the distal portion, the fixation element configured to attach to a septal wall of a patient's heart, the elongate body configured to transfer torque from the proximal portion to the distal portion;
   an implantable lead comprising a proximal portion, a distal portion, a lead body extending between the proximal portion and the distal portion, and an electrode coupled to the distal portion, the distal portion configured to be at least partially inserted into the septal wall, the electrode configured to be implanted at an implantation site in the septal wall, wherein the implantable lead is slidably coupled to and rotatable relative to the fixation member,
   wherein the elongate body of the fixation member defines a lumen extending from the proximal portion to the distal portion of the fixation member, wherein the lumen is configured to receive the implantable lead such that the implantable lead is slidably and rotatably movable through the proximal portion and the distal portion of the fixation member during implantation of the implantable lead while the fixation member is attached to the septal wall; and
   a securing member to couple the proximal portion of the fixation member and the proximal portion of the implantable lead after implantation of the implantable lead to mitigate migration of the implantable lead.

2. The system of claim 1, wherein the fixation element comprises a helix to screw in or out of the septal wall in response to rotation of the fixation member.

3. The system of claim 1, wherein the fixation element is electrically conductive and electrically coupled to the proximal portion of the fixation member.

4. The system of claim 1, wherein the elongate body comprises a braided structure.

5. The system of claim 4, wherein the braided structure comprises a conductor electrically coupled to the fixation element.

6. The system of claim 1, wherein the elongate body comprises a porous region to allow fluid communication between an outside and an inside of the elongate body.

7. The system of claim 1, wherein the implantable lead comprises multiple electrodes coupled to the lead body.

8. The system of claim 7, wherein the implantable lead comprises one or more electrically insulated coil conductors electrically coupled to the multiple electrodes.

9. The system of claim 7, wherein each of the multiple electrodes are independently electrically coupled to a therapy delivery circuit of an implantable medical device.

10. The system of claim 7, wherein when the implantable lead is implanted, at least one of the electrodes is not implanted in the septal wall.

11. The system of claim 1, wherein the implantable lead defines an inner lumen to receive a guide wire.

12. The system of claim 11, wherein the electrode of the implantable lead defines at least part of the inner lumen.

13. The system of claim 12, further comprising a sealing element coupled to the electrode of the implantable lead to form a fluid seal between the guide wire and an inner surface of the electrode.

14. The system of claim 1, wherein the distal portion of the implantable lead comprises a tapered structure in a screw configuration, wherein the tapered structure comprises the electrode.

15. The system of claim 1, further comprising telescoping delivery catheters defining catheter lumens to receive the fixation member and the implantable lead and to position the fixation member and the implantable lead proximate to the septal wall, wherein the telescoping delivery catheters comprise an outer catheter and an inner catheter slidably coupled to and rotatable relative to the outer catheter.

16. The system of claim 1, wherein the electrode of the implantable lead comprises a segmented electrode including two or more segments angularly spaced from one another.

* * * * *